(12) United States Patent
Naing et al.

(10) Patent No.: US 12,037,150 B2
(45) Date of Patent: Jul. 16, 2024

(54) APPARATUS AND METHOD FOR MONITORING AND CONTROLLING THE ASEPTIC FILLING AND SEALING OF PHARMACEUTICAL CONTAINERS WITH A PHARMACEUTICAL FLUID USING ROTARY STAGE

(71) Applicant: Vanrx Pharmasystems Inc., Burnaby (CA)

(72) Inventors: Juvenal Naing, Belcarra (CA); Yakov Gofman, Richmond (CA); Marcin Cichy, Surrey (CA); John Senger, New Westminster (CA); Craig Rathe, Vancouver (CA); Carlos Alberto Diaz Guerrero, Burnaby (CA)

(73) Assignee: VANRX PHARMASYSTEMS INC., Burnaby (CA)

( * ) Notice: Subject to any disclaimer, the term of this patent is extended or adjusted under 35 U.S.C. 154(b) by 27 days.

(21) Appl. No.: 17/588,610

(22) Filed: Jan. 31, 2022

(65) Prior Publication Data

US 2023/0242285 A1    Aug. 3, 2023

(51) Int. Cl.
*B65B 3/00* (2006.01)
*A61L 2/20* (2006.01)
(Continued)

(52) U.S. Cl.
CPC ............... *B65B 3/003* (2013.01); *A61L 2/20* (2013.01); *B65B 43/60* (2013.01); *B65B 55/18* (2013.01);
(Continued)

(58) Field of Classification Search
CPC ......... B65B 3/003; B65B 43/60; B65B 55/18; A61L 2/20; A61L 2202/122; A61L 2202/14
See application file for complete search history.

(56) References Cited

U.S. PATENT DOCUMENTS 3,292,342 A    12/1966  Kapeker
3,712,021 A    1/1973   Logemann
(Continued)

FOREIGN PATENT DOCUMENTS

CN    102100637 A    6/2011
CN    103193001 A    7/2013
(Continued)

OTHER PUBLICATIONS

United States Patent and Trademark Office, Non-Final Office Action (U.S. Appl. No. 15/264,554, which is a Divisional of U.S. Appl. No. 15/264,554, a parent of the present application), Date of Issuance: Feb. 7, 2022.
(Continued)

*Primary Examiner* — Andrew M Tecco
*Assistant Examiner* — Nicholas E Igbokwe
(74) *Attorney, Agent, or Firm* — Kevin R. Erdman; Brannon Sowers & Cracraft PC

(57) ABSTRACT

The system of the invention involves a gloveless aseptic processing system. The automated system is for filling nested pharmaceutical containers with a pharmaceutical fluid substance. A closed sterilizable gloveless isolator chamber is capable of maintaining an aseptic condition, having a sterilization system. The container filling system has a dispensing head for filling the containers, and a container closing system disposed within the gloveless isolator chamber with rams for pushing closures into openings of the nested containers. The container manipulation mechanism is disposed within the gloveless isolator chamber and is capable of positioning the nested pharmaceutical containers within the gloveless isolator chamber including operably disposing the nested pharmaceutical containers with the container filling system and the container closing system. Container tubs sealed by removable covers and contain a (Continued)

container nest bearing a plurality of pre-sterilized pharmaceutical containers.

26 Claims, 17 Drawing Sheets

(51) Int. Cl.
  *B65B 43/60* (2006.01)
  *B65B 55/18* (2006.01)
(52) U.S. Cl.
  CPC ..... *A61L 2202/122* (2013.01); *A61L 2202/14* (2013.01)

(56) References Cited

U.S. PATENT DOCUMENTS

| | | | |
|---|---|---|---|
| 3,770,119 A | 11/1973 | Hultberg | |
| 3,954,174 A | 5/1976 | Kraus | |
| 4,444,310 A * | 4/1984 | Odell | A61M 5/002 206/366 |
| 4,754,175 A | 6/1988 | Kobayashi | |
| 4,757,175 A | 7/1988 | Mohr | |
| 5,519,984 A * | 5/1996 | Beussink | B65B 7/2821 53/489 |
| 6,189,292 B1 | 2/2001 | Odell | |
| 7,096,896 B2 | 8/2006 | Py | |
| 7,783,383 B2 | 8/2010 | Eliuk | |
| 7,937,907 B2 | 5/2011 | Fleckenstein | |
| 8,511,045 B2 | 8/2013 | Mastio | |
| 8,842,280 B2 | 9/2014 | Yamamoto | |
| 9,862,519 B2 | 1/2018 | Deutschle et al. | |
| 2003/0092288 A1 | 5/2003 | Yamamoto | |
| 2004/0129590 A1 | 7/2004 | Petricca | |
| 2005/0160704 A1 | 7/2005 | Miksch | |
| 2005/0252176 A1 * | 11/2005 | Pritchard | B65D 33/008 53/469 |
| 2006/0048844 A1 * | 3/2006 | Merrill | A61L 9/00 141/85 |
| 2006/0219359 A1 | 10/2006 | Miyamoto | |
| 2006/0259195 A1 * | 11/2006 | Eliuk | B01F 33/8442 700/245 |
| 2008/0017311 A1 | 1/2008 | Yoshioka | |
| 2008/0087353 A1 * | 4/2008 | Py | B65B 37/06 141/130 |
| 2009/0202332 A1 * | 8/2009 | Trebbi | B65B 59/04 414/788 |
| 2009/0208316 A1 | 8/2009 | Mayer | |
| 2009/0223592 A1 * | 9/2009 | Procyshyn | B65B 3/003 141/2 |
| 2010/0058711 A1 | 3/2010 | Blumenstock | |
| 2010/0180551 A1 | 7/2010 | Duethorn | |
| 2010/0281829 A1 | 11/2010 | Leu | |
| 2011/0024419 A1 | 2/2011 | Gabel | |
| 2011/0146841 A1 | 6/2011 | Ansaloni et al. | |
| 2011/0202063 A1 | 8/2011 | Bonnin | |
| 2012/0090268 A1 | 4/2012 | Krauss | |
| 2012/0110952 A1 | 5/2012 | Zardini | |
| 2013/0001117 A1 | 1/2013 | Liversidge | |
| 2013/0240552 A1 | 9/2013 | Thomas | |
| 2013/0281961 A1 | 10/2013 | Ray | |
| 2013/0340390 A1 | 12/2013 | Carson | |
| 2014/0092937 A1 | 4/2014 | Albright | |
| 2014/0196411 A1 * | 7/2014 | Procyshyn | B65B 7/2821 141/1 |
| 2015/0232228 A1 | 8/2015 | Weissbrod | |
| 2016/0200461 A1 * | 7/2016 | Broadbent | B65B 55/027 53/426 |
| 2016/0206870 A1 | 7/2016 | Albright | |
| 2018/0072446 A1 | 3/2018 | Naing | |
| 2019/0016492 A1 | 1/2019 | Guerrero | |
| 2019/0111435 A1 | 4/2019 | Gong | |

FOREIGN PATENT DOCUMENTS

| | | |
|---|---|---|
| CN | 105271086 | 1/2016 |
| CN | 109803895 B | 11/2021 |
| DE | 102006039120 A1 | 3/2008 |
| EP | 2192042 A1 | 6/2010 |
| EP | 2812163 A2 | 12/2014 |
| JP | 061394 H | 11/1994 |
| JP | 2012017137 | 1/2012 |
| WO | 2013156851 A2 | 10/2013 |
| WO | 2013156851 A3 | 10/2013 |
| WO | 2015023924 A2 | 2/2015 |
| WO | 2017072591 A1 | 5/2017 |

OTHER PUBLICATIONS

Brazil Patent Office Search Report (BR112019004866 which claims priority to PCT/CA2017/051071, claiming priority to U.S. Appl. No. 15/264,554 which is a parent application of the present application). Date of Issuance: Dec. 28, 2021.
United States Patent and Trademark Office, Notice of Allowance for U.S. Appl. No. 17/005,178 (which is a Divisional of a Continuation-in-Part of the parent of the present application), Date of Issuance: Jul. 14, 2022.
United States Patent and Trademark Office, Non-Final Office Action (U.S. Appl. No. 16/370,526 which is a parent application of the present application), Date of Issuance: Dec. 9, 2022.
Canadian Intellectual Property Office, PCT International Search Report (PCT/CA2017/051071), Date of Issuance: Nov. 23, 2017.
Canadian Intellectual Property Office, Written Opinion of the International Searching Authority, International Application No. PCT/CA2017/051071, dated Dec. 11, 2017.
European Patent Office, European Search Report (EP/17849957), Date of Issuance: Aug. 13, 2020.
European Patent Office, Examination of the European Searching Authority, European Application No. EP/17849957, dated Jun. 16, 2020.
United States Patent and Trademark Office, Non-Final Office Action (U.S. Appl. No. 15/264,554), Date of Issuance: Dec. 16, 2021.
China National Intellectual Property Administration Office Action and Search Report (Chinese national stage of PCT/CA2017/051071), corresponding to the subject matter of the present application. Date of Mailing: Sep. 6, 2022.
European Patent Office, Examination Report for application EP17 849 957.0, Mar. 10, 2023, which is based on the priority application of the present application.
United States Patent and Trademark Office, Final Office Action (U.S. Appl. No. 15/264,554 which is a parent application of the present application), Date of Issuance: Jul. 1, 2022.
European Patent Office, Supplementary European Search Report and ANNEX for application EP19800042, Dec. 20, 2021, involving technology of the assignee of the present application.

* cited by examiner

APPARATUS AND METHOD FOR MONITORING AND CONTROLLING THE ASEPTIC FILLING AND SEALING OF PHARMACEUTICAL CONTAINERS WITH A PHARMACEUTICAL FLUID USING ROTARY STAGE

CROSS-REFERENCE TO RELATED APPLICATIONS

This application is continuation application of U.S. patent application Ser. No. 17/005,178, filed Aug. 27, 2020; which is a divisional application of U.S. patent application Ser. No. 15/647,633, filed Jul. 12, 2017, now U.S. Pat. No. 10,710,758; which is a continuation-in-part of U.S. patent application Ser. No. 15/465,516, filed Mar. 21, 2017, now U.S. Pat. No. 10,524,980; which is a continuation-in-part of copending U.S. patent application Ser. No. 15/264,554, filed Sep. 13, 2016; and also claims priority to copending U.S. patent application Ser. No. 15/818,986, filed Nov. 21, 2017; the disclosures of which are herein incorporated by reference in their entireties.

BACKGROUND OF THE INVENTION

Field of the Invention

This present invention relates to the medical field as exemplified by IPC class A61 and more particularly to apparatus and associated methods for sterilization of and sterile handling of pharmaceutical materials and containers for pharmaceuticals, including bringing pharmaceuticals into form for administration to medical or veterinary patients. In one aspect, it relates to the programmed and automatic operation of such apparatus.

Background

The subject of filling pharmaceuticals into pharmaceutical containers is a major aspect of the Pharmaceuticals Industry. The subject is heavily controlled by various governmental and official bodies in various countries. Technologically, the subject is a challenge in that the pharmaceutical products need to be filled into the containers under very strict aseptic conditions. Very specific procedures are specified for this task to a degree that makes the handling of pharmaceuticals profoundly different from the handling of any other industrial product, including specifically semiconductors, which also demand extreme and consistent environmental conditions. Indeed, the parallels between the handling of semiconductors in semiconductor "clean laboratories" and the handling of pharmaceuticals in aseptic isolators are superficial. They share the use of such "clean laboratories", but there is no inherent aseptic requirement associated with semiconductor manufacture.

The filling of pharmaceutical containers with fluid pharmaceuticals specifically requires the aseptic handling of both the containers and the fluid pharmaceutical itself. This leads to complex mechanisms and procedures, many of which may be automated to one degree or another. Often, the production equipment for fluid pharmaceutical handling is bulky and expensive. This creates a problem for smaller operations, particularly in the small-scale production and development environments. As the field has developed, the need for smaller, more compact equipment, particularly in the filling and compounding of fluid pharmaceuticals, has become evident.

The prior art is typically characterized by the use of vibratory bowls and escapements. Many prior art systems also employ gloves for use by the operator to access the interior of the chamber.

SUMMARY OF THE INVENTION

In one general aspect, the invention features a method for filling nested pharmaceutical containers with a pharmaceutical fluid substance, such as a liquid, solution, or suspension having therapeutic properties. The method includes providing a filling system comprising a sterilizable chamber capable of maintaining an aseptic condition, with the chamber comprising a filling station and a planar rotary stage having a destination fiducial locating structure including constraining surfaces. The method also includes transferring into the chamber at least one container tub sealed by a container tub cover and containing a container nest bearing a plurality of pharmaceutical containers, aseptically sealing the chamber, and establishing an aseptic condition within the chamber. The container nest bearing the plurality of pharmaceutical containers is transferred into the destination fiducial locating structure such that the container nest is held in place by the constraining surfaces, and the pharmaceutical fluid substance is dispensed into at least a portion of the plurality of pharmaceutical containers by operating both the rotary stage and the filling station.

In some embodiments the operating the filling station may include rotating the filling station. The dispensing the pharmaceutical fluid substance may comprise dispensing the pharmaceutical fluid substance on an iterative and serial basis into the containers. Providing a filling system may comprise providing a filing apparatus comprising at least one cover removal station within the chamber, with the transferring into the destination fiducial locating structure the container nest comprising removing the container tub cover from the container tub by operating both the rotary stage and the at least one cover removal station. Operating the at least one cover removal station may comprise rotating the at least one cover removal station. Providing the filling system may comprise providing within the chamber at least one cover removal station having an engagement tool, transferring into the chamber at least one container tub may comprise attaching to the container tub cover a cover removal fixture, and operating the at least one cover removal station may comprise engaging the engagement tool with the cover removal fixture.

The method may further comprise transferring into the chamber a container closure tub sealed by a container closure tub cover and containing at least one container closure nest bearing a plurality of pharmaceutical container closures. The method may further comprise positioning one of the at least one closure nests to align closures in the at least one closure nest with corresponding containers in the container nest, transferring the nests of aligned closures and containers to the ramming station by rotating the rotary stage, and forcing the closures into the corresponding containers. Positioning one of the at least one closure nests may comprise obtaining image information about the one of the at least one closure nest, and positioning the one of the at least one closure nests based on the image information.

Positioning one of the at least one closure nest may comprise applying a vacuum to suction cups, lifting the container closure nest with the suction cups, and operating the rotary stage. Transferring into the destination fiducial locating opening the container nest may comprise applying a vacuum to suction cups, lifting the container nest with the suction cups, and operating the rotary stage. Dispensing the pharmaceutical fluid substance may comprise simultaneously and/or serially operating the rotary stage and the filling station, and removing the container tub cover may comprise simultaneously and/or serially operating the rotary stage and the at least one cover removal station.

In another general aspect, the invention features a system for filling nested pharmaceutical containers with a pharmaceutical fluid substance comprising a sterilizable chamber capable of maintaining an aseptic condition. The chamber includes a filling station, and a planar rotary stage having a rotary stage rotation axis and comprising a destination fiducial locating structure including constraining surfaces disposed and shaped to receive and hold a pharmaceutical container nest bearing a plurality of pharmaceutical containers.

In further embodiments the filling station may comprise a fluid product dispenser head, with the filling station being configured to be rotatable about a filling station rotation axis parallel to the rotary stage rotation axis to position in combination with rotation of the rotary stage the dispenser head over any one of the plurality of pharmaceutical containers held in the container nest in the destination fiducial locating structure. The chamber may further comprise at least one cover removal station and the rotary stage may further comprise a first source fiducial locating structure including constraining surfaces disposed and shaped to receive and hold a pharmaceutical container closure tub sealed by a container closure tub cover and containing at least one pharmaceutical container closure nest bearing a plurality of pharmaceutical container closures, and at least one second source fiducial locating opening disposed and shaped to receive and hold a pharmaceutical container tub sealed by a container tub cover and containing a pharmaceutical container nest bearing a plurality of pharmaceutical containers.

The at least one cover removal station may be disposed and configured to be rotatable about a cover removal station rotation axis parallel to the rotary stage rotation axis to remove in combination with rotation of the rotary stage the container tub cover from the at least one container tub and the container closure tub cover from the container closure tub. At least one cover removal station may comprise an engagement tool disposed and configured to engage with engagement fixtures pre-attached to the container tub cover and to the container closure tub cover.

The system may further comprise at least one camera disposed to obtain image information about at least one of the container nest and the closure nest, and a controller, with the chamber further comprising at least one vacuum pickup system comprising suction cups disposed to engage with the container nests and the container closure nests, the at least one vacuum pickup system being configured in combination with rotation of the rotary stage to lift a pharmaceutical container nest from a pharmaceutical container tub held in one of the at least one second source fiducial locating openings and to deposit the pharmaceutical container nest in the destination fiducial locating opening in combination with rotation of the rotary stage and to lift a pharmaceutical container closure nest from a pharmaceutical container closure tub held in the first source fiducial locating opening and to deposit the container closure nest on top of the pharmaceutical container nest under control of the controller.

The controller may be operative to instruct the at least one camera to provide to the controller the image information and the controller may be operative to control the rotation of the rotary stage to place the closures in the closure nest in correspondence with containers in the container nest. The system may further comprise a ram system configured for forcing the closures into the corresponding containers.

The system may further comprise at least one rotatable cover removal station having a cover removal station rotation axis parallel to the rotary stage rotation axis, at least one vacuum pickup system for placing the container closure nest on the container nest with closures in the closure nest in correspondence with containers in the container nest, and a ram system for forcing the closures into the containers, with the filing station being a rotatable filling station having a filling station rotation axis parallel to the rotary stage rotation axis and comprising a fluid product dispenser head. The system may further comprise at least one camera for obtaining image information of at least one of the container nest and the closure nest, and a controller comprising a memory and a processor. The controller may be operative to instruct the rotary stage to rotate to angular positions that are one of predetermined and based on the image information and to control the at least one cover removal station, the filling station, the at least one vacuum pickup system, and the ram system to operate in conjunction with the rotary stage.

In a further general aspect, the invention features a system for filling nested pharmaceutical containers with a pharmaceutical fluid substance that includes means for establishing and maintaining an aseptic condition in a chamber, means for constraining a container nest bearing a plurality of pharmaceutical containers in the chamber, and means for transferring a container nest to the means for constraining from a container tub in the chamber. It also includes means for rotating the means for constraining in the chamber; and means for dispensing the pharmaceutical fluid substance into at least a portion of the plurality of pharmaceutical containers in the container nest while the container nest is constrained by the means for constraining.

In a further aspect, a system is provided for filling nested pharmaceutical containers with a pharmaceutical fluid substance, the system comprising a sterilizable chamber capable of maintaining an aseptic condition, the chamber comprising: a planar rotary stage having a rotary stage rotation axis, a plurality of locating structures positioned with respect to the rotary stage at different positions around the rotary stage rotation axis, for holding nests of pharmaceutical container parts at the different positions around the rotary stage rotation axis, and a container filling station having a dispensing head for filling the containers while they are held in a nest at one of the locating structures. The locating structures may include surfaces associated with a first tub-holding opening in the rotary stage for holding a first tub containing at least one nest of containers, surfaces associated with a second tub-holding opening in the rotary stage for holding a second tub containing at least one nest of closures, and surfaces associated with a destination nest-holding opening in the rotary stage for holding at least one nest.

The chamber may further comprise at least one vacuum pickup system comprising suction cups disposed to engage with the container nest and container closure nest held on the rotary stage, the at least one vacuum pickup system being configured in combination with rotation of the rotary stage to lift a pharmaceutical container nest from a pharmaceutical container tub and to deposit the pharmaceutical container nest in the destination opening in combination with rotation of the rotary stage and to lift a pharmaceutical container closure nest from a pharmaceutical container closure tub and to deposit the container closure nest on top of the pharmaceutical container nest.

At least one of the locating structures may include a reconfigurable locating structure with one or more adjustable positioning surfaces to position a tub with respect to the rotary stage. The reconfigurable locating structure may include at least one pair of a reconfigurable stopping member and a restraining member disposed opposite each other across an opening in the rotary stage to precisely position at a first predetermined position a tub that contains at least one nest. The stopping member may be adjustable to stop the tub at the first predetermined position by a rotary adjustment and the restraining member may be disposed to restrain the tub in the first predetermined position.

At least a first of the reconfigurable locating structures may include a rotary positioning element having an axis of rotation parallel to a plane of the rotary stage and includes a plurality of different positioning surfaces that are selectable by rotating the rotary positioning element. At least one of the reconfigurable locating structures may include a pair of opposing rotary positioning elements each having an axis of rotation parallel to a plane of the rotary stage and each may include a plurality of different positioning surfaces that are selectable by rotating the rotary positioning elements to accommodate different nest widths.

At least one of the reconfigurable locating structures may include at least a first pair of opposing positioning elements that define positioning surfaces that oppose each other along a first positioning axis that is at least generally parallel to a plane of the rotary stage and at least a second pair of opposing positioning elements that define positioning surfaces that oppose each other along a second positioning axis that is at least generally parallel to a plane of the rotary stage and at least generally perpendicular to the first positioning axis. The at least one of the positioning elements in each of the first and second pairs of positioning elements may include a rotary positioning element having an axis of rotation parallel to a plane of the rotary stage and including a plurality of different positioning surfaces.

The system may further include a reconfigurable vacuum pickup system comprising: a first set of suction cups arranged in a first pattern, a second set of suction cups arranged in a second pattern different from the first pattern, and a selection mechanism operative to position either the first set of suction cups or the second set of suction cups to engage with the at least a first of the nests of pharmaceutical container parts while it is held by one of the plurality of locating structures. The selection mechanism of the reconfigurable vacuum pickup system may include a rotary mechanism operative to position the first or second sets of suction cups in an engagement position.

The system may further include at least one cover removal station positioned to remove covers from tubs containing at least one nest of pharmaceutical packaging materials held in one of the locating structures. The at least one cover removal station may be rotatable about a cover removal station rotation axis parallel to the rotary stage rotation axis to remove the tub covers in combination with rotation of the rotary stage. The at least one cover removal station may comprises an engagement tool disposed and configured to engage with a cover removal fixture on the tub cover.

The filling station may be configured to be rotatable about a filling station rotation axis parallel to the rotary stage rotation axis to position in combination with rotation of the rotary stage the dispenser head over any one of the plurality of pharmaceutical containers held by one of the one of the locating structures.

The system may further comprise at least one camera disposed to obtain image information about at least one of the nests of pharmaceutical container parts. The system may further comprise a ram system configured for forcing nested closures into corresponding nested containers.

The system may further comprise at least one rotatable cover removal station having a cover removal station rotation axis parallel to the rotary stage rotation axis; at least one vacuum pickup system for placing a container closure nest on a container nest with closures in the closure nest in correspondence with containers in the container nest; a ram system for forcing the closures into the containers; and wherein the filing station is a rotatable filling station having a filling station rotation axis parallel to the rotary stage rotation axis and comprising a fluid product dispenser head.

The system may further comprise at least one camera for obtaining image information of at least one of the container nest and the closure nest, a controller comprising a memory and a processor, and wherein the controller is operative to instruct the rotary stage to rotate to angular positions that are one of predetermined and based on the image information and to control the at least one cover removal station, the filling station, the at least one vacuum pickup system, and the ram system to operate in conjunction with the rotary stage.

In another aspect, a system is provided for filling nested pharmaceutical containers with a pharmaceutical fluid substance, comprising: means for establishing and maintaining an aseptic condition in a chamber; means for constraining a container nest bearing a plurality of pharmaceutical containers in the chamber; means for transferring to the means for constraining a container nest from a container tub in the chamber; means for rotating the means for constraining in the chamber; and means for dispensing the pharmaceutical fluid substance into at least a portion of the plurality of pharmaceutical containers in the container nest while the container nest is constrained by the means for constraining.

In a further aspect, a method is provided for filling nested pharmaceutical containers with a pharmaceutical fluid substance, the method comprising: providing a filling system comprising a sterilizable chamber capable of maintaining an aseptic condition, the chamber comprising a filling station and a planar rotary stage having a destination locating structure; transferring into the chamber at least one container tub sealed by a container tub cover and containing a container nest bearing a plurality of pharmaceutical containers; aseptically sealing the chamber; establishing an aseptic condition within the chamber; transferring into the destination locating structure the container nest bearing the plurality of pharmaceutical containers such that the container nest is held in place; and dispensing the pharmaceutical fluid substance into at least a portion of the plurality of pharmaceutical containers by operating both the rotary stage and the filling station. The operating the filling station may include rotating the filling station. The dispensing the pharmaceutical fluid substance may comprise dispensing the pharmaceutical fluid substance on an iterative and serial basis into the containers.

The providing a filling system may comprise providing a filing apparatus comprising at least one cover removal station within the chamber and wherein the transferring into the destination locating structure the container tub comprises removing the container tub cover from the container tub by operating both the rotary stage and the at least one cover removal station. The operating the at least one cover removal station may comprise rotating the at least one cover removal station. The providing the filling system may comprise providing within the chamber at least one cover removal station having an engagement tool, the transferring into the chamber at least one container tub may comprise attaching to the container tub cover a cover removal fixture; and wherein the operating the at least one cover removal station comprises engaging the engagement tool with the cover removal fixture.

The method may further comprise transferring into the chamber a container closure tub sealed by a container closure tub cover and containing at least one container closure nest bearing a plurality of pharmaceutical container closures. The method may further comprise positioning one of the at least one closure nests to align closures in the at least one closure nest with corresponding containers in the container nest; transferring the nests of aligned closures and containers to a ramming station by rotating the rotary stage; and forcing the closures into the corresponding containers. The method may further include adjusting a tub locating structure to accommodate a size of the closure nest tub. The positioning one of the at least one closure nest may comprise: obtaining image information about the one of the at least one closure nests; and positioning the one of the at least one closure nests based on the image information. The positioning one of the at least one closure nest may comprise: applying a vacuum to suction cups; lifting the container closure nest with the suction cups; and operating the rotary stage.

The transferring into the destination locating opening the container nest may comprise: applying a vacuum to suction cups; lifting the container nest with the suction cups; and operating the rotary stage. The method may further include selecting one of a plurality of sets of suction cups and wherein the applying a vacuum to suction cups is performed for the selected set of suction cups. The selecting may include rotating one of the plurality of sets of suction cups into position. The method may further include the destination locating structure to accommodate a size of the container nest. The adjusting may be performed in two at least generally orthogonal directions. The method may further include adjusting a tub locating structure to accommodate a size of the container nest tub.

In another general aspect, the invention features a container assembly for holding nested pharmaceutical container parts. It includes a container comprising a bottom, a top lip that provides a horizontal top sealing surface that has a peripheral outline, and sidewalls located between the bottom and the top lip. It also includes a peelable container cover consisting of a sheet of flexible material sealed to the sealing surface of the top lip of the rectangular container to seal the contents of the container, and a cover removal fixture on the container cover.

The sealed peelable container cover may include a portion that extends outside of the peripheral outline of the top sealing surface of the container, and the cover removal fixture may be on the portion of the peelable container cover that extends outside of the peripheral outline of the top sealing surface of the container. The container may be rectangular and includes four sidewalls. The cover removal fixture may include an appendage to allow it to be engaged by an engagement tool. The cover removal fixture may include a ball-shaped appendage to allow it to be engaged by an engagement tool. The peelable container cover may be heat sealed to the sealing surface of the top lip of the rectangular container to seal the contents of the container against decontamination. The peelable container cover may be sealed to the sealing surface of the top lip of the rectangular container to seal the contents of the container against decontamination using a chemical agent. The peelable container cover may sealed to the sealing surface of the top lip of the rectangular container to seal the contents of the container against decontamination using a radiation. The peelable container cover may be sealed to the sealing surface of the top lip of the rectangular container to seal the contents of the container against decontamination using plasma. The peelable cover may be made of a plastic material. The peelable cover may be made of an impermeable laminated foil. The peelable cover may be made of a polymeric membrane. The cover removal fixture may be clipped to a portion of the peelable container cover that extends outside of the peripheral outline of the top sealing surface of the container. The sealed container may hold sterilized pharmaceutical containers or closures.

In a further aspect, a method is provided for removing within a controlled environment enclosure a container cover from a sealed container, the sealed container being sealed by the container cover, the method comprising: providing the container in the controlled environment enclosure with the cover sealed to a sealing surface of a lip of the container to seal the contents of the container against decontamination, the cover having a cover removal fixture, decontaminating the sealed container in the controlled environment enclosure, engaging the cover removal fixture with an engagement tool, and removing the cover from the container using the engagement tool. The engaging may engage the cover removal fixture with a fork-shaped engagement tool. The engaging may engage a ball-shaped appendage on the cover removal fixture.

The providing may include providing sterilized pharmaceutical containers or closures in the sealed container before the decontaminating. The attaching may take place before the container is in the controlled environment enclosure. The decontaminating the sealed container in the controlled environment enclosure may take place before the removing the cover. The removing the cover may include moving the engagement tool relative to the container. The removing the cover may include moving both the container and the engagement tool. The method may further comprise attaching the cover removal fixture to the cover before providing the container in the controlled environment enclosure.

In a further aspect, a method is provided for removing within a sterilizable environment a cover from a tub sealed with the cover, the method comprising: providing a sterilizable chamber capable of maintaining an aseptic condition; holding in the chamber a tub sealed with a peelable cover, the tub and cover having corresponding pluralities of corners; illuminating one or more peeling monitor zones proximate the cover removal station with light from at least one light source; peeling the cover from one of the plurality of corners of the tub; measuring a first intensity of light from the illuminating at one of the peeling monitor zones proximate to and substantially non-overlapping with the tub and after at least a portion of the peeling; assessing a current status of the peeling of the cover from the tub based on the first intensity of light; and providing an indication of the assessed current status. The measuring a first intensity of light may comprise measuring a first intensity of light from the light source diffusely reflected from the one of the peeling monitor zones.

The method may further comprise deciding a next step in the removing process based on the current status of the peeling. The assessing a current status of the peeling of the cover from the one of the plurality of corners of the tub may comprise comparing the first light intensity with a first predetermined light intensity value. The assessing a current status of the peeling of the cover from the one of the plurality of corners of the tub may comprise detecting the cover blocking light from the illuminating in the one of the peeling monitor zones.

The method may further comprise, if the one of the plurality of corners of the tub is the last of the plurality of corners being peeled, detaching the cover completely from the tub; measuring a last intensity of light from the illuminating at the one of the peeling monitor zones; and assessing the detaching of the cover from the tub based on the last intensity of light and the first intensity of light. The assessing the detaching of the cover from the tub may comprise comparing the last intensity of light with a last predetermined light intensity value. The measuring the last intensity of light may comprise measuring light from the light source diffusely reflected from the one of the peeling monitor zones.

The peeling monitor zones may on a movable platform and the peeling the cover from the one of the plurality of corners of the tub may comprise moving the platform. The providing the sterilizable chamber may comprise providing a sterilizable chamber comprising a planar rotary stage having a source locating structure to perform the holding of the tub, and the peeling the cover from the one of the plurality of corners of the tub may comprise rotating the planar rotary stage. The providing the sterilizable chamber may comprise providing a movable platform having a source locating structure to perform the holding of the tub, and the peeling the cover from the one of the plurality of corners of the tub may comprise moving the platform.

The providing the chamber may comprise providing a cover removal station comprising an engagement tool and the peeling may comprise: attaching a cover removal fixture to the tub cover before placing the tub in the source locating structure; engaging the cover removal fixture with the engagement tool; and moving the engagement tool. The providing the sterilizable chamber may comprise providing a sterilizable chamber comprising a planar rotary stage having a source locating structure to perform the holding of the tub, and the peeling the cover from the one of the plurality of corners of the tub may comprise rotating the planar rotary stage.

In a further aspect a system is provided for automatically monitoring and controlling the removing within a sterilizable environment of a cover sealed to a tub, the tub and cover having corresponding pluralities of corners, the system comprising: a sterilizable chamber capable of maintaining an aseptic condition, the chamber comprising: a source locating structure disposed to hold the tub in a fixed position, a cover removal station disposed to engage with the cover and to peel the cover from the tub, a peeling monitor surface positioned proximate the cover removal station, one or more light sources disposed to illuminate at least a portion of the peeling monitor surface, and one or more light sensors sensitive to light from the light source and disposed to preferentially collect and measure light diffusely reflected from the illuminated portion of the peeling monitor surface. The system may further comprise a controller in communication with the cover removal station, the light source and the light sensor. The light source may be an infrared light source and the sensor may be an infrared sensor.

The controller may comprise a memory and software instructions which when loaded in the memory and executed by the controller cause the controller to operate the cover removal station, the light source and the light sensor. The peeling monitor surface may be part of a surface of a movable platform; and the software instructions when loaded in the memory and executed by the controller may further cause the controller to be able to move the platform. The movable platform may be a planar rotary stage having a rotary stage rotation axis. At least one of the cover removal station and the platform may operable to peel the cover from one of the plurality of corners of the tub and to move a peeled portion of the cover into a peeling monitor zone, the peeling monitor zone being within the illuminated portion of the platform, proximate the tub and substantially non-overlapping with the tub.

The sensor may be configurable for measuring a first intensity of light from the light source diffusely reflected from the peeling monitor zone; and the software instructions when loaded in the memory and executed by the controller may further enable the controller to: operate at least one of the light sources and at least one of the sensors to measure the first intensity of light immediately after the peeled portion of the cover has been moved into the peeling monitor zone; assess a current status of the peeling of the cover from the tub based on the first intensity of light; and determine a next step in the removing based on the current status of the peeling. A first predetermined light intensity value may be stored in the memory and the software instructions when loaded in the memory and executed by the controller may further enable the controller to assess a current status of the peeling of the cover from the tub by comparing the first light intensity with the first predetermined light intensity value.

If the first of the plurality of corners of the tub is the last of the plurality of corners being peeled the software instructions when loaded in the memory and executed by the controller may further enable the controller to: operate at least one of the cover removal station and the platform to detach the cover completely from the tub; operate at least one of the light sources and at least one of the sensors to measure a last intensity of light from the light source diffusely reflected from the peeling monitor zone; and assess the detaching of the cover from the tub based on the last intensity of light and the first intensity of light. A last predetermined light intensity value may be stored in the memory; and the software instructions when loaded in the memory and executed by the controller may further enable the controller to assess the detaching of the cover from the tub by comparing the last light intensity with the last predetermined light intensity value.

Systems and methods according to the invention need not employ either vibratory bowls or escapements. Nor do such systems or method require gloves. Systems and methods according to the invention may therefore address needs for compact, small-scale filling and compounding of fluid pharmaceuticals.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein.

Figure 1A:
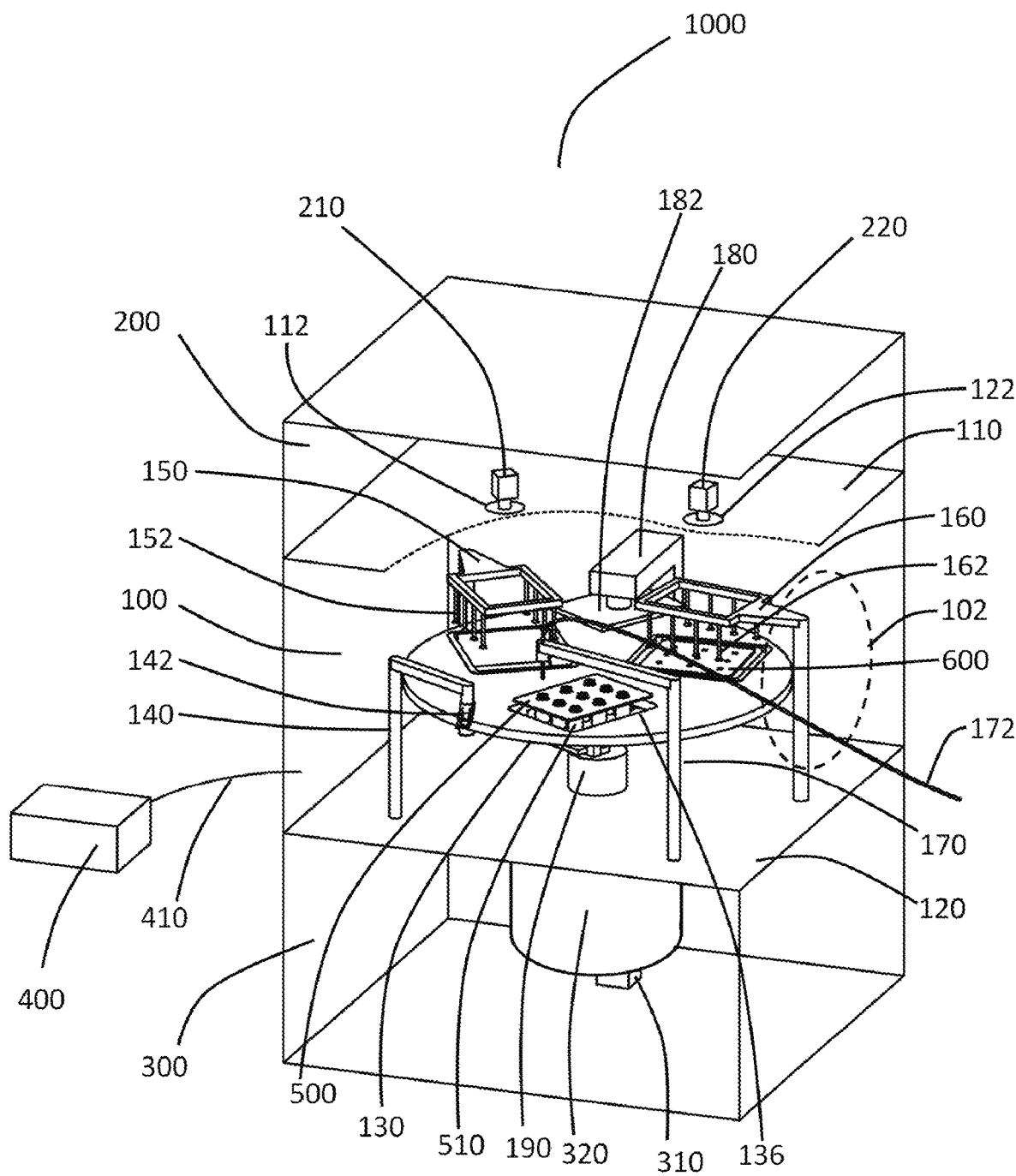
FIG. 1A is a drawing of an apparatus for filling pharmaceutical containers with a pharmaceutical fluid product. For the sake of clarity some surfaces are shown in cutaway form and others are shown as transparent.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts are also representative in nature, and actual embodiments of the invention may include further features or steps not shown in the drawings. The exemplifications set out herein illustrate embodiments of the invention, in one or more forms, and such exemplifications are not to be construed as limiting the scope of the invention in any manner.

DETAILED DESCRIPTION

The embodiments disclosed below are illustrative and not intended to be exhaustive or limit the invention to the precise form disclosed in the following detailed description. Rather, the embodiments are chosen and described so that others skilled in the art may utilize their teachings.

The present invention relates to an apparatus and method for filing pharmaceutical containers with a pharmaceutical fluid substance in a spatially constrained environment. In FIG. 1A, filling system 1000 comprises sealable chamber 100 in communication with an ambient environment, sealable chamber 100 being capable of having an aseptic environment established within its interior and capable of maintaining that aseptic environment within its interior. The interior of sealable chamber 100 may be rendered aseptic by any one or more of a number of treatments, including but not limited to treatment with a sterilant, such as steam, hydrogen peroxide vapor, ozone, nitrogen dioxide, and ethylene oxide. The structures and mechanisms to perform such sterilization steps are well known in the art and are not shown in FIG. 1A.

Chambers 200 and 300 are separated from chamber 100 by upper wall 110 and lower wall 120 respectively and are not required to be capable of maintaining aseptic environments within their interiors. The communication of chamber 100 with the ambient environment may be via suitable aseptically sealable access door 102, schematically shown in broken outline in FIG. 1A. Suitable sealable doors and ports are well known in the art and will not be dwelt upon further in this specification. The ambient environment may be, for example, a clean room adapted for the handling of pharmaceuticals during production. Since space is at a premium in such spatially constrained clean environments, there is much merit in reducing the so-called "footprint" of equipment to be housed in the clean environment.

The terms "aseptic" and "sterilize" and their derivatives are to be understood as follows for the purposes of the present specification. Establishing an aseptic condition in the interior of a chamber shall be understood to mean establishing that condition throughout the internal atmosphere of the chamber as well as on substantially all exposed interior surfaces of the chamber. This shall include the surfaces of all items, containers, subsystems and the like exposed to the interior atmosphere of the chamber. To the extent that extremely tight crevices or microscopic crevices may exist in the interior of the chamber such that a sterilizing gas or vapor may not perfectly penetrate into such tight regions, for example, the degree of sterilization in practical cases may not be total. This is acknowledged in both the industry and in the standards set for the industry. The action of establishing an aseptic condition within the interior of the chamber and "sterilizing the interior of the chamber" shall have the same meaning in this specification.

Introducing into the interior of a chamber with an aseptic condition an item of which the surfaces are not suitably sterilized destroys the existing aseptic condition within the chamber. Conversely, introducing an aseptic or sterilized item into an interior of a chamber that does not have an aseptic condition within that interior does not render that interior aseptic. In fact, all it does is to destroy the aseptic condition of the surface of the item so introduced. Similarly, introducing filtered air, even with all biological entities filtered out, into an unsterilized chamber does not in any way sterilize the chamber or render it aseptic to a degree acceptable in the pharmaceutical industry. The reason is that the interior surfaces of the chamber are not sterilized by the introduction of such air. All that is achieved is to contaminate the filtered air with active biological species resident on the interior surfaces of the unsterilized chamber.

In the interest of clarity and completeness, it should also be recorded that in the art the term "aseptic" is also sometimes used in association with the introduction of pharmaceutical fluids along aseptic tubes into bodies within controlled chambers. In such cases the term in the art refers to the condition inside the tube or to the fact that the pharmaceutical fluid may be filtered to a suitable degree. This in no way sterilizes or renders aseptic the interior of the chamber in question. The aseptic condition in such cases is confined to the interior of the tube bearing the pharmaceutical stream. Such streams are often filtered to a high degree, but such filtering affects only the interior of the particular tube and does not in any way sterilize the interior of the chamber.

In some prior art systems, containers introduced into a chamber for the purposes of being filled with a pharmaceutical are routed through sterilizing subsystems. This kills biological species on the containers. When such sterilized containers are introduced into the chamber when the chamber itself is not aseptic the containers lose their aseptic condition as biological species contained within the chamber will deposit on the previously aseptic containers.

It should also be pointed out that pharmaceutical or semiconductor clean rooms of any quality level, including "Class 100", "Class 10" or "Class 1", even when employing laminar flow hoods and the like or any quality of HEPA (High Efficiency Particulate Air) filters or ULPA (Ultra Low Particulate Air) filters, cannot constitute an aseptic chamber because they do not have an assurable means to render the surfaces of the room sterile or aseptic. Standards for clean rooms exist from both the United States Federal Government and ISO (International Standards Organization). These specify in great detail to different standards the allowed particulate content of a cubic volume of air in such a clean room facility. None of these standards address the matter of biological species present on surfaces in the room. This serves to make the point that a chamber cannot be rendered aseptic by the management of its atmosphere or airflow only. Nor, conversely, may the chamber be rendered aseptic by the sterilization of only the surfaces of its interior.

The text "Guideline for Disinfection and Sterilization in healthcare Facilities, 2008" by Rutala et al from the Center for Disease Control lists a compendium of mechanisms and methods for sterilization. Our concern in this specification is specifically with those mechanisms for sterilizing the interior of a chamber; that is, sterilizing both the interior surfaces and the atmosphere within the chamber. Given the requirements, vapor base methods are most appropriate to the task. These include, but are not limited to, treatment with heated water vapor, hydrogen peroxide vapor, ozone, nitrogen dioxide, ethylene oxide, glutaraldehyde vapor or other suitable sterilizing gases and vapors. In one suitable method appropriate to the present invention, the sterilization is by means of hydrogen peroxide vapor which is then flushed using ozone before the chamber is employed in the filling of pharmaceutical containers.

The subsystems of the apparatus 1000 contained with sealable chamber 100 will now be described at the hand of FIG. 1A to FIG. 1G. Due to the compactness and density of components and subsystems of apparatus 1000, certain components and subsystems are omitted from the drawings of FIG. 1B to FIG. 1G in the interest of clarity and the focus is placed on components and subsystems most relevant to the supporting text in this specification. Planar rotary stage 130 is fully rotatable through 360 degrees in a horizontal plane parallel to lower wall 120 about rotary stage rotation axis 131 and may be raised and lowered by means of bellows feed-through 190. The use of bellows feed-through 190 allows chamber 100 to retain its aseptic condition during the motion of rotary stage 130. A suitable engine and gearing system 320 may be housed within chamber 300. Engines, for example stepper motors, as well as gearing systems suitable for rotating rotary stage 130 with suitable angular precision and repeatability are well known in the art and are not further discussed in this specification.

Figure 1B:
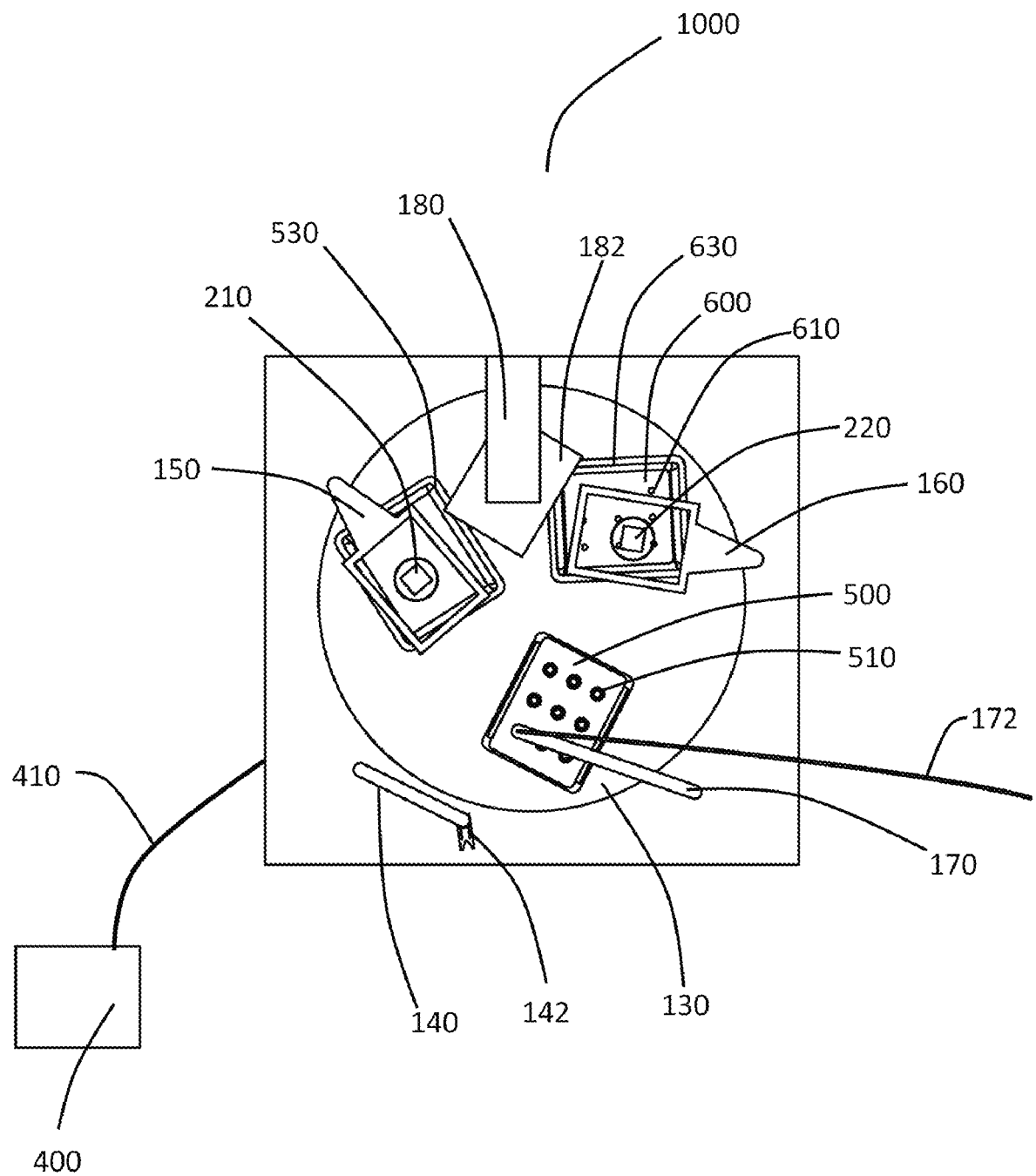
FIG. 1B is a plan view of one chamber of the apparatus of FIG. 1A.
Figure 1C:
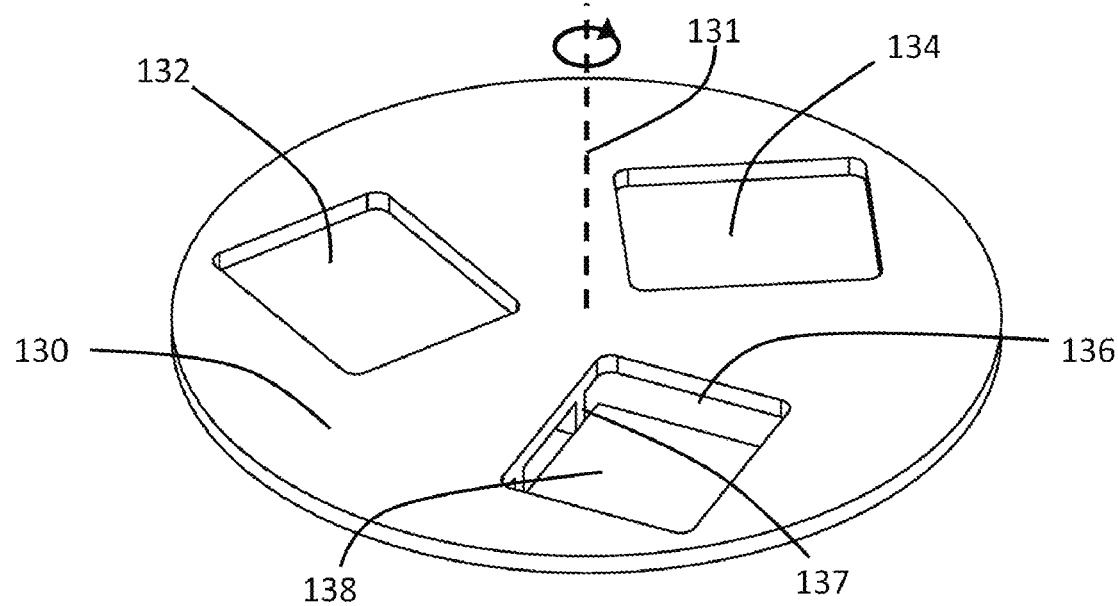
FIG. 1C shows a rotary stage of the apparatus of FIG. 1A and FIG. 1B.

As shown in FIG. 1C, at least three fiducial locating openings 132, 134, and 136 are provided in rotary stage 130. Fiducial locating opening 132 is employed for receiving container tubs 530 holding sterilized pharmaceutical containers 510 pre-packed in a predetermined pattern in container nests 500. Container tubs 530 are typically substantially rectangular and are sealed with peelable covers 520. Suppliers of pharmaceutical containers provide their product in this format to users of the apparatus of the present specification. Fiducial locating opening 134 is employed for receiving container closure tubs 630 holding sterilized pharmaceutical containers closures 610 pre-packed in a predetermined pattern in container closure nests 600. Container closure tubs 630 are typically substantially rectangular and are sealed with peelable tub covers not shown in FIG. 1A to FIG. 1G. The peelable covers of tubs 630 are functionally identical to peelable covers 520. Suppliers of pharmaceutical containers provide their product in this format to users of the apparatus of the present specification. In the interest of the compactness of system 1000, the rectangular axes of locating openings 132, 134, and 136 may be oriented at an angle with respect to the radial direction of rotary stage 130 in order to ensure a suitably small radius for rotary stage 130.

Suitable container nests 500 and container closure nests 600; container tubs 530 and container closure tubs 630; and peelable tub covers 520 are described in published United States Patent Application US 2016-0200461, the specification of which is hereby incorporated in full. Alternative cover gripping arrangements for the removal of tub covers from tubs are also described in published United States Patent Application US 2016-0251206, the specification of which is hereby incorporated in full.

In the interest of clarity, FIG. 1A to FIG. 1G show, and the associated text to follow below will describe, the use of single tub 530 of pharmaceutical containers 510 along with single tub 630 of container closures 610. In practice, container closures 610 are provided as multiple nests 600 per container closure tub 630. To this end rotary stage 130 may contain more than one fiducial locating opening 132 to each receive a respective one of container tub 530 holding sterilized pharmaceutical containers 510 pre-packed in container nest 500. In yet other implementations, more than one nest 500 of containers 510 may be present in a single pharmaceutical container tub 530.

Fiducial locating opening 136 is specifically arranged to receive container nests 500 bearing pharmaceutical containers 510. Whereas tubs 530 and 630 naturally locate in fiducial locating openings 132 and 134 and are suspended by their own rims once in opening 132 and 134, containers 510 are correctly located in opening 136 and retained in position by some other mechanism. To this end, fiducial locating opening 136 comprises four fiducial retaining guides 137. Baseplate 138 is located within fiducial locating opening 136 as a loose component of system 1000, and rests on the horizontal portions at the bottoms of each of four fiducial retaining guides 137 (see FIG. 1C and FIG. 1D). This arrangement allows baseplate 138 to move freely, guided by fiducial retaining guides 137. We shall return to this arrangement when discussing the closing of containers with container closures.

Figure 1D:
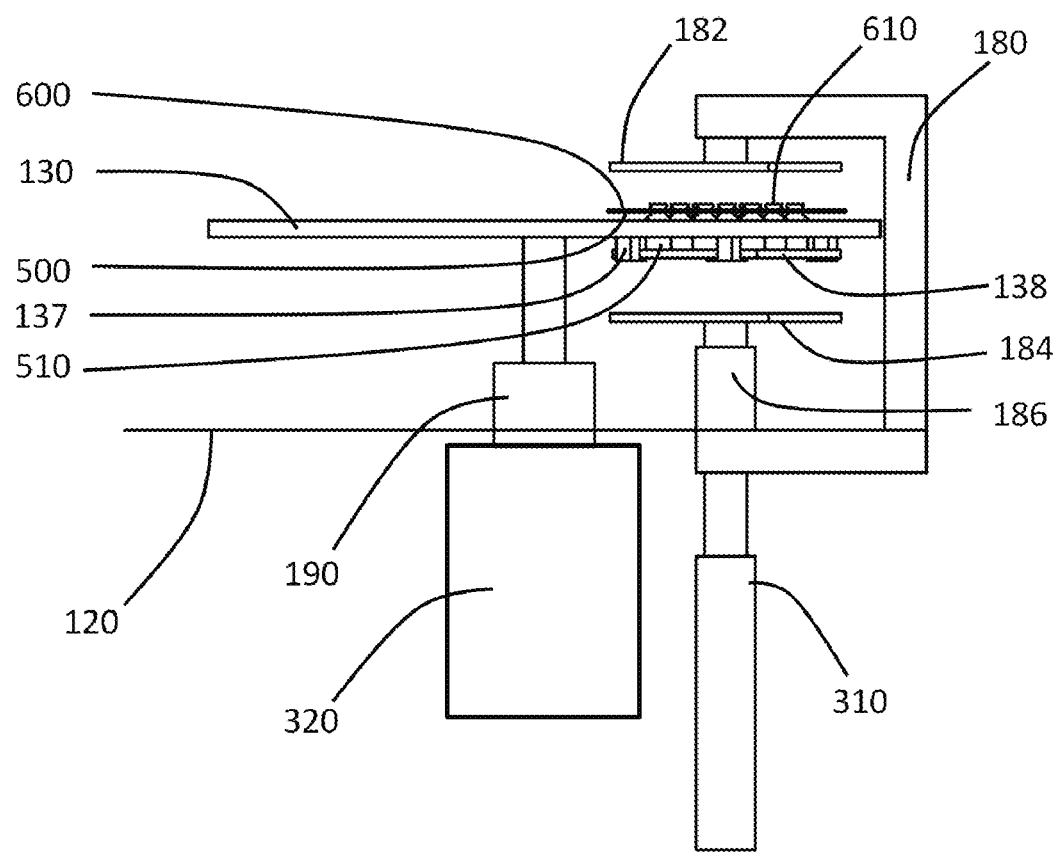
FIG. 1D shows a side view of a portion of the apparatus of FIG. 1A and FIG. 1B.
Figure 1E:
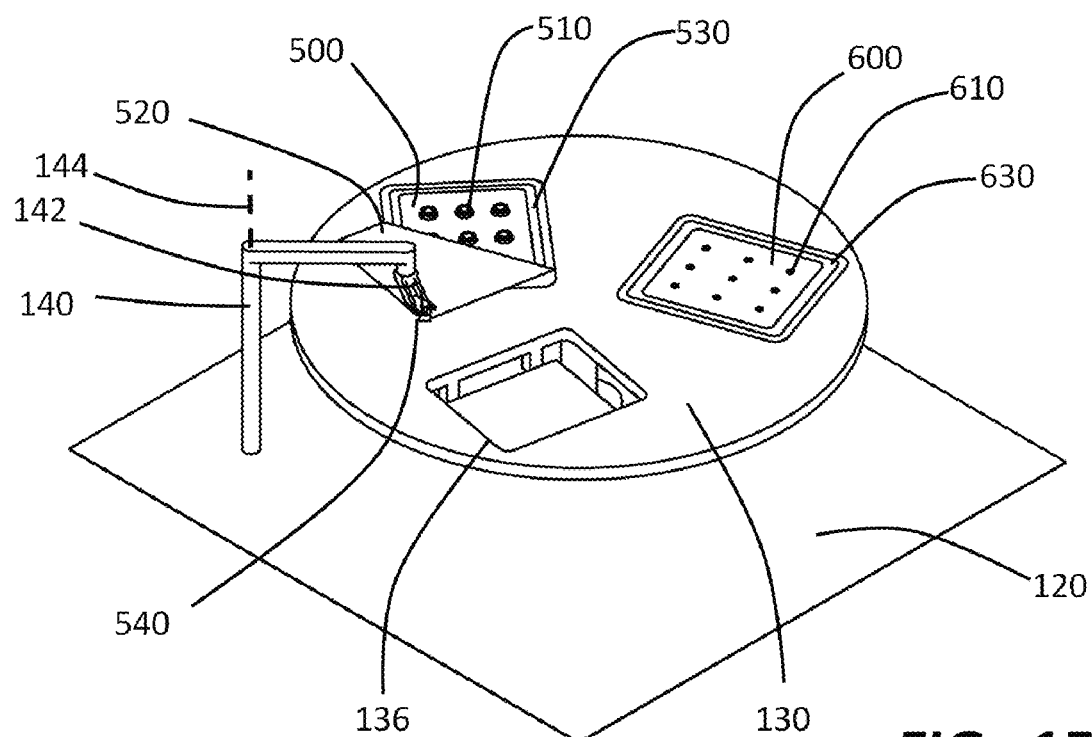
FIG. 1E shows a pharmaceutical container tub cover seated in the rotary stage of FIG. 1A to FIG. 1D being removed.

FIG. 1E shows fiducial locating opening 136 as empty, while cover 520 is being peeled from container tub 530 in fiducial locating opening 132 (not visible) to expose nest 500 bearing pharmaceutical containers 510. At this point in the operation of system 1000, a cover similar to cover 520 has already been pealed from tub 630 in fiducial locating opening 134 (not visible) to expose nest 600 bearing container closures 610. FIG. 1G shows a close-up detailed view of the peeling of cover 520. Cover removal station 140 is rotatable about cover removal station rotation axis 144 parallel to rotary stage rotation axis 131 and comprises engagement tool 142, which, in this particular embodiment, is fork-shaped in order to engage with cover removal fixture 540 attached to cover 520. Cover removal fixture 540 is pre-attached to cover 520 before tub 530 is transferred into system 1000 via door 102 (See FIG. 1A). In the embodiment shown in FIG. 1E and FIG. 1G, cover removal fixture 540 is clipped to cover 520 and has a ball-shaped appendage to allow it to be engaged by engagement tool 142. Other combinations of cover removal fixtures and engagement tools are contemplated and system 1000 is not limited to the particular combination of cover removal fixture and engagement tool shown in FIG. 1A, FIG. 1E and FIG. 1G. Cover removal fixture 540, for example, may be manufactured as an integral part of cover 520 for use in filling systems such as filling system 1000. Or it may be clipped to cover 520 during the placement into tub 530 of nests 500 bearing containers 530 and during the placement into tub 630 of nests 600 bearing container closures 610.

Rotary stage 130 may be lowered to assist in obtaining a less acute angle between cover 520 and tub 530. Too acute an angle may lead to the tearing of cover 520. Cover removal station 140 may be rotated while rotary stage 130 rotates so that the combined motions of cover removal station 140 and rotary stage 130 provide a low stress path for the removal of cover 520, thereby limiting the chances of tearing of cover 520. In particular, cover removal station 140 may be rotated to ensure that engagement tool 142 is not present above fiducial locating opening 132 when container tub 530 is placed in or removed from fiducial locating opening 132.

In some embodiments, system 1000 comprises single cover removal station 140 for sequentially removing covers from tubs 520 and 620. In other embodiments, system 1000 may be equipped with two or more cover removal stations 140 for dedicated removal of covers from tubs 520 and 620 and other additional tubs. In some embodiments covers are simultaneously removed from tubs 520 and 620 and from other tubs, all the removal processes benefiting from a single rotary motion of rotary stage 130.

Figure 1F:
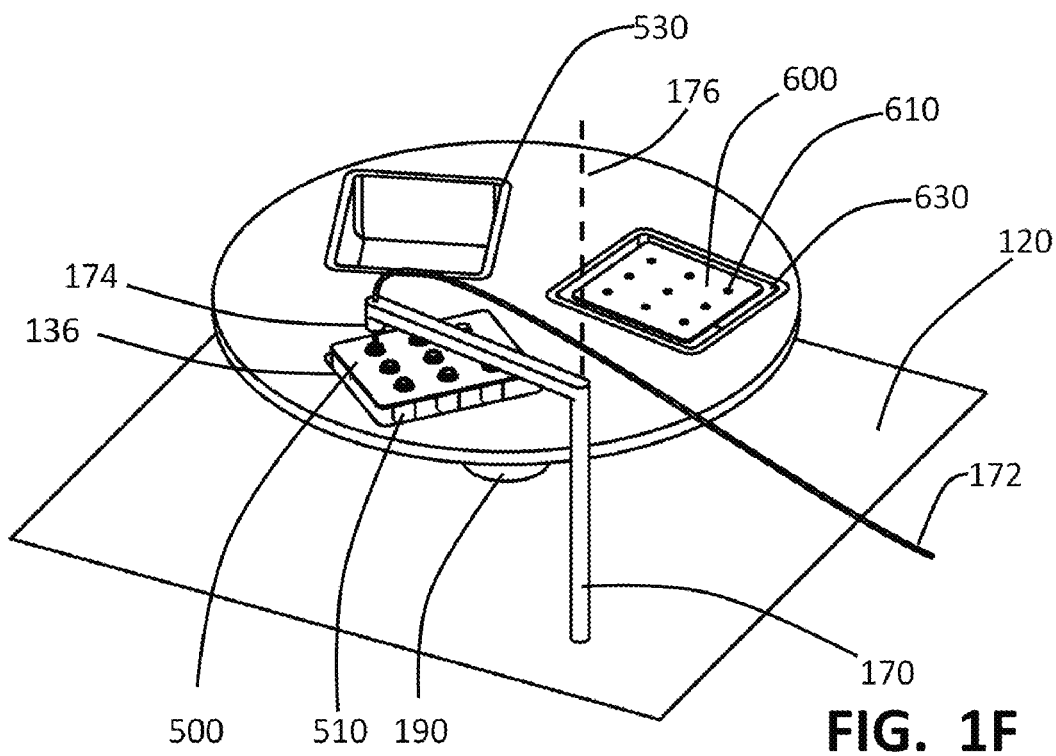
FIG. 1F shows pharmaceutical containers being filled with a pharmaceutical fluid substance in the apparatus of FIG. 1A to FIG. 1E.
Figure 1G:
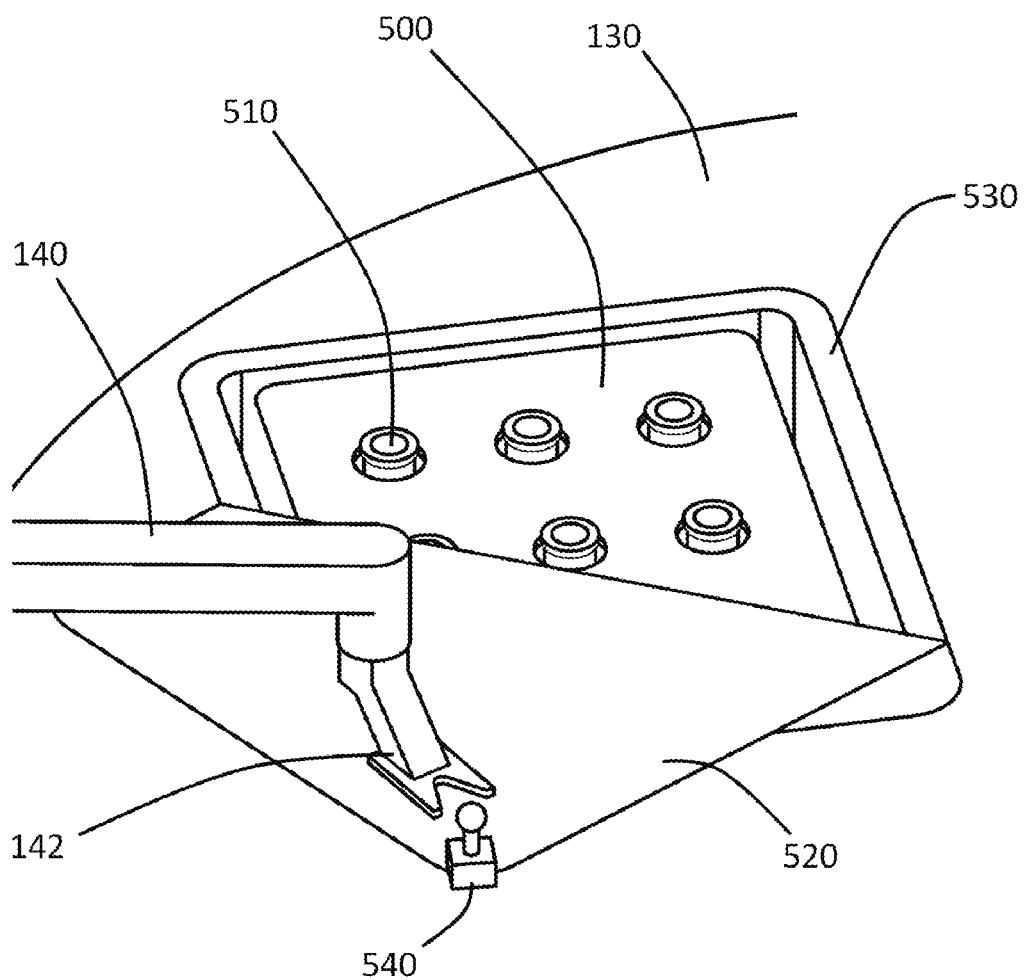
FIG. 1G provides a more detailed view of the cover removal components of the apparatus of FIG. 1A, FIG. 1B and FIG. 1E.

In FIG. 1A, FIG. 1B, and FIG. 1F filling station 170 for filling pharmaceutical containers 510 with pharmaceutical fluid product comprises pharmaceutical fluid product feed line 172 supplying pharmaceutical fluid product to a pharmaceutical fluid product dispenser head 174 (See FIG. 1F). Filling station 170 is rotatable about filling station rotation axis 176 parallel to rotary stage rotation axis 131. Filling station 170 and rotary stage 130 may simultaneously or sequentially rotate to place dispenser head 174 over an opening of any selected container 510 in nest 500 when nest 500 is seated in fiducial locating opening 136. This allows every container 510 in nest 500 to be filled with pharmaceutical fluid product by product dispenser head 174. When not engaged in filling containers 510, filling station 170 may be rotated to swing dispenser head 174 completely away from fiducial locating opening 136, thereby allowing nests 600 bearing container closures 610 to be placed on top of nest 500 with closure 610 directly on top of an opening of every container 510 residing in fiducial locating opening 136.

Another term employed to describe dispenser head 174 is "filling needle". Suitable filling needles and protective sheathing arrangements for such filling needles are described in published United States Patent Applications US 2016-0346777 and US 2017-0121046, the specifications of which are hereby incorporated in full.

FIG. 1A and FIG. 1B show two vacuum pickup systems 150 and 160, each respectively comprising a plurality of suction cups 152 and 162 (See FIG. 1B). Vacuum pickup system 150 is arranged to pick up nests 500 of containers 510 by means of suction cups 152, and vacuum pickup system 160 is arranged to pick up nests 600 of containers 610 by means of suction cups 162. Vacuum pickup system 160 may be raised and lowered in order to allow suction cups 162 to engage with different nests 600 of container closures 610 contained at differing depths inside tub 630. To this end, vacuum pickup system 160 may comprise a bellows feed-through allowing vertical motion whilst maintaining the aseptic integrity of chamber 100. Suitable vacuum pumps, or vacuum lines from a vacuum source external to system 1000, may be connected to vacuum pickup systems 150 and 160, and ensure suitable vacuum at the suction cups 152 and 162.

Cameras 210 and 220 are disposed to view and record the positioning of suction cups 152 and 162 on nests 500 and 600 respectively. In the embodiment shown in FIG. 1A, cameras 210 and 220 are disposed within chamber 200 and view nests 500 and 600 through sealed windows 112 and 122 respectively. In other embodiments, cameras 210 and 220 may be disposed within chamber 100 and view nests directly from within chamber 100.

Container closing ram system 180, shown in FIG. 1A, FIG. 1B, and FIG. 1D, comprises upper ram plate 182 disposed within chamber 100 above rotary stage 130, lower ram plate 184 disposed within chamber 100 below rotary stage 130, and ram drive 310 within chamber 300. Ram drive 310 is disposed for driving lower ram plate 184 vertically toward upper ram plate 182 via bellows feed-through 186. Loose base plate 138 of fiducial locating opening 136, when located above lower ram plate 184 by suitably rotating rotary stage 130, is pushed upward by ram plate 184 and is guided in the process by the fiducial retaining guides 137 (See FIG. 1D). When closures 610 in closure nest 600 are ultimately pushed against upper ram plate 182, they are forced into the openings of containers 510 in nest 500. This creates a sandwiched nest of closed containers 510, each closed by a corresponding closure 610. As shown in FIG. 1D, nests 500 and 600 are forced together in the process to create a compound nest 500/600.

Controller 400, shown in FIG. 1A and FIG. 1B, may communicate with the rest of system 1000 via control communications line 410, or may be contained physically within system 1000, for example, within chamber 200. Controller 400 may have suitable memory and a processor containing suitable software programming instructions which, when loaded in the memory executed by the processor, control the motions of ram system 180, vertical motion and rotating action of rotary stage 130, the application of vacuum to vacuum pickup systems 150 and 160, the imaging by cameras 210 and 220, the vertical motion of vacuum pickup system 160, any rotational or vertical motions required from cover removal stations 140 and filling station 170, as well as the on-and-off valving of the pharmaceutical fluid product supply to dispenser head 174. Suitable valves and pumps, typically peristaltic pumps, required for the pharmaceutical fluid product supply to dispenser head 174 are well known in the art and may be housed in chamber 200 or may be located outside system 1000. The various mechanical drives for the subsystems described above are well-known in the art, will not be discussed here in detail. These may typically be housed in chamber 200 of system

1000. The software, when executed by the processor, instructs the rotary stage to rotate to angular positions that are either predetermined or based on image information from the cameras and controls the cover removal stations, the filling station, the vacuum pickup systems, and the ram system to operate specifically in conjunction with the rotary stage.

Figure 2A:
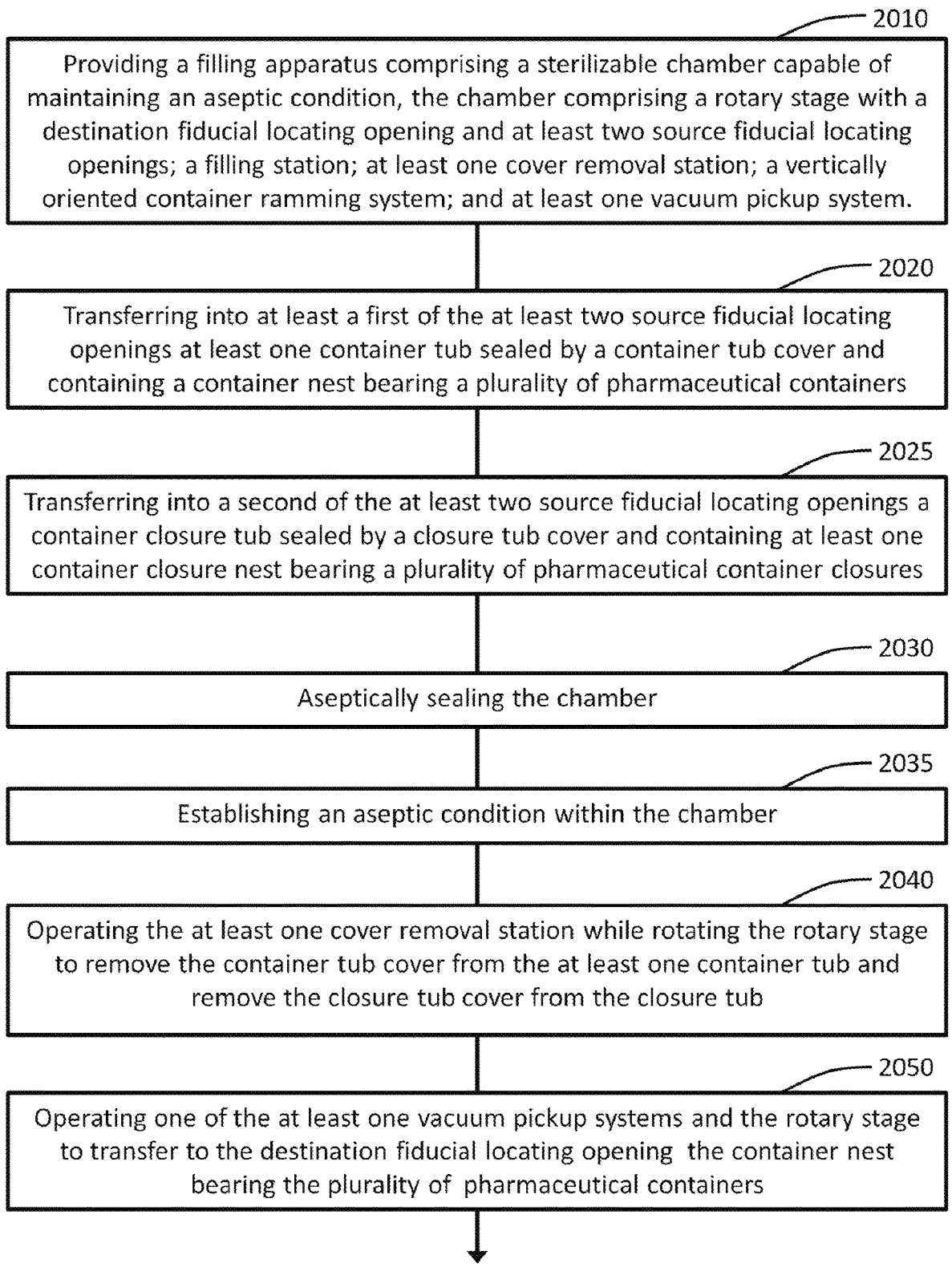
FIG. 2A and FIG. 2B jointly form a drawing of a flow chart for a method of aseptically filling pharmaceutical containers with a pharmaceutical fluid substance in a spatially constrained environment.
Figure 2B:
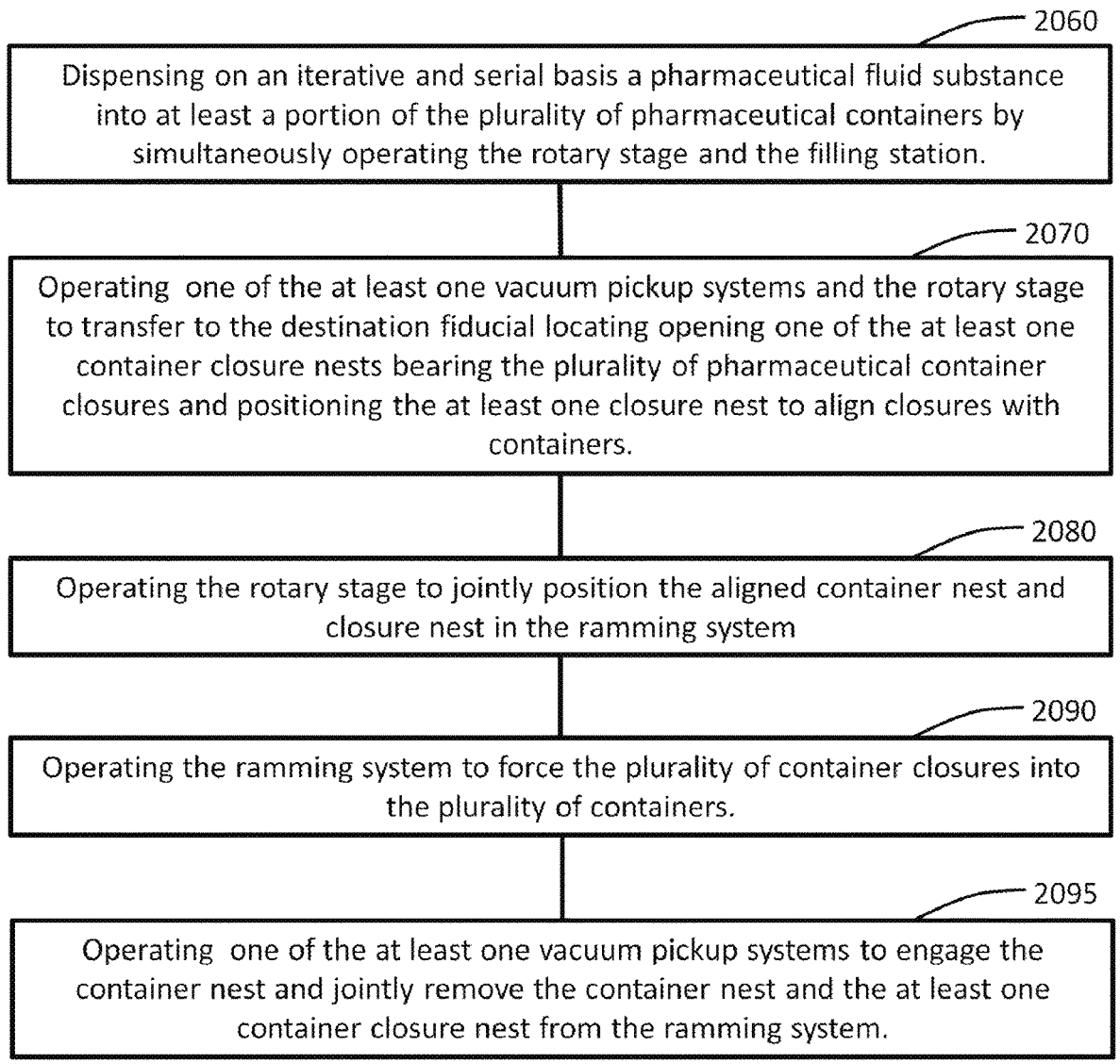

A method based on system 1000 for filling nested pharmaceutical containers with a pharmaceutical fluid product will now be described at the hand of the flow chart given in FIG. 2A, and which is continued in FIG. 2B. The method comprises providing [2010] filling apparatus 1000 comprising sterilizable chamber 100 capable of maintaining an aseptic condition, the chamber comprising rotary stage 130 with destination fiducial locating opening 136 and at least two source fiducial locating openings (132 and 134); filling station 170; at least one cover removal station 140; vertically oriented container ramming system 180; and at least one vacuum pickup system (for example 150 and/or 160). The method further comprises transferring [2020] into at least a first of the at least two source fiducial locating openings (132 and 134) at least one container tub 530 sealed by container tub cover 520 and containing container nest 500 bearing a plurality of pharmaceutical containers 510; and transferring [2025] into a second of the at least two source fiducial locating openings (134 and 132) container closure tub 630 sealed by a closure tub cover and containing at least one container closure nest 600 bearing a plurality of pharmaceutical container closures 610.

The method further comprises aseptically sealing [2030] the chamber 100 and establishing [2035] an aseptic condition within the chamber 100. The establishing [2035] an aseptic condition within chamber 100 may comprise treating the interior of chamber 100 with any one or more of steam, hydrogen peroxide vapor, ozone, nitrogen dioxide, and ethylene oxide.

The method further comprises operating [2040] the at least one cover removal station 140 and rotating rotary stage 130 to remove container tub cover 520 from the at least one container tub 530 and remove closure tub cover from closure tub 630; operating [2050] rotary stage 130 and one of the at least one vacuum pickup systems (for example 150 and/or 160) to transfer to destination fiducial locating opening 136 container nest 500 bearing the plurality of pharmaceutical containers 510; and dispensing [2060] on an iterative and serial basis a pharmaceutical fluid substance into at least a portion of the plurality of pharmaceutical containers 510 by operating rotary stage 130 and filling station 170. The phrase "iterative and serial" is employed in this specification to describe the fact that the same operational steps are repeatedly used to fill the various containers and the fact that the containers are filled one after another, as opposed to simultaneously. In some embodiments multiple containers may be simultaneously filled using a filling station with multiple dispenser heads.

Steps [2040], [2050], and [2060] each involves rotating rotary stage 130 and operating another device, being respectively cover removal station 140, one of the at least one vacuum pickup systems (for example 150 and/or 160), and filling station 170. The motions involved may be simultaneous in some cases or embodiments, and serial in other cases or embodiments. In some embodiments some of the motions may be simultaneous and others may be serial.

The operating [2040] the at least one cover removal station 140 may comprise engaging an engagement tool (for example tool 142) with a cover removal fixture (for example fixture 540) pre-attached to the cover being removed. Operating [2050] one of the at least one vacuum pickup systems may comprise contacting container nest 500 with a plurality of suction cups 152 while applying a vacuum to suction cups 152. The dispensing [2060] a pharmaceutical fluid substance into at least a portion of the plurality of pharmaceutical containers may comprise disposing on an iterative and serial basis fluid product dispenser head 174 of filling station 170 over the openings of the at least a portion of the plurality of pharmaceutical containers 510. The operating [2050] rotary stage 130 and one of the at least one vacuum pickup systems may comprise operating camera 210 to obtain image information of container nest 500 bearing the plurality of pharmaceutical containers 510 and to position the one of the at least one vacuum pickup systems over container nest 500.

The method further comprises operating [2070] one of the at least one vacuum pickup systems (for example 150 and/or 160) and rotary stage 130 to transfer to destination fiducial locating opening 136 one of the at least one container closure nests 600 bearing the plurality of pharmaceutical container closures 610 and positioning the at least one closure nest 600 to align closures 610 with containers 510; operating [2080] rotary stage 130 to jointly position aligned container nest 500 and closure nest 600 in ramming system 180; and operating [2090] ramming system 180 to force the plurality of container closures 610 into the plurality of containers 510.

Operating [2070] one of the at least one vacuum pickup systems may comprise contacting container closure nest 600 with a plurality of suction cups 162 while applying a vacuum to suction cups 162. Operating [2090] ramming system 180 may comprise driving the plurality of pharmaceutical containers 510 toward upper ram plate 182 of ramming system 180.

Operating [2070] rotary stage 130 and one of the at least one vacuum pickup systems may comprise operating camera 220 to obtain image information of the one of the at least one container closure nests 600 bearing the plurality of pharmaceutical container closures 610 and to position the one of the at least one vacuum pickup systems over the one of the at least one container closure nests 600.

Providing [2010] a filling apparatus may comprise providing a filling apparatus further comprising controller 400 and a software program executable by controller 400. Any one or more of aseptically sealing [2030] chamber 100; establishing [2035] an aseptic condition within chamber 100; operating rotary stage 130; operating the at least one cover removal station 140; operating [2070] one of the at least one vacuum pickup systems (150 and/or 160); operating filling station 170; and operating [2090] ramming system 180 may be done automatically by executing the software program in the controller.

In the embodiment described at the hand of FIGS. 1A to 1F, each of steps [2040], [2050], [2060], [2070], and [2080] comprises rotating a rotary stage, for example rotary stage 130, bearing the container nests and container closure nests.

In other embodiments a plurality of the steps of removing a container tub cover from at least one container tub 530; removing a container tub cover from at least one container closure tub 630; transferring to destination fiducial locating opening 136 container nest 500; dispensing a pharmaceutical fluid substance into pharmaceutical containers 510; transferring to destination fiducial locating opening 136 one of the at least one container closure nests 600; and positioning aligned container nest 500 and closure nest 600 in ramming system 180 comprises rotating a rotary stage bearing the container nests and container closure nests.

In a general embodiment, at least one of the steps of removing a container tub cover from at least one container tub 530; removing a container tub cover from at least one container closure tub 630; transferring to destination fiducial locating opening 136 container nest 500; dispensing a pharmaceutical fluid substance into pharmaceutical containers 510; transferring to destination fiducial locating opening 136 one of the at least one container closure nests 600; and positioning aligned container nest 500 and closure nest 600 in ramming system 180 comprises rotating a rotary stage bearing the container nests and container closure nests.

It is to be noted that neither filling system 1000, nor the associated method, needs to employ the vibratory bowls or escapements that are typical of the prior art. Unlike many prior art systems, filling system 1000 also does not require the use of gloves for use by the operator to access the interior of the chamber.

The system above has been described as employing a controller that runs stored software running on a general-purpose computer platform, but it may also be implemented in whole or in part using special-purpose hardware.

The system described above also employs fiducial openings defined in the rotary stage to hold the tubs and nests, but it may also employ other types of fiducial structures that include other configurations of constraining surfaces sufficient to hold the tubs and nests in place. Notched posts mounted on the rotary stage may hold the tubs and/or nests above the rotary stage, for example. Further fiducial locating structures for holding tubs of nests for containers or container closures will be described below at the hand of FIGS. 3A, 3B, 4A, and 5A.

As shown in FIG. 7 and FIG. 8A-D, filling system 1000 may comprise peeling monitor sensor 230 disposed to collect light from a source fiducial locating opening, for example 132 or 134, when fiducial locating opening 132 or 134 is located proximate cover removal station 140 to allow the removal of a cover from a tub located in source fiducial locating opening 132 or 134. Peeling monitor sensor 230 may be located behind sealed window 124 separating sensor 230 from sealable chamber 100. Peeling monitor sensor 230 may be a CCD camera or any other light sensor that is addressable or configurable via software or other suitable means to provide a total light signal from a pre-defined portion of its field of view.

In FIGS. 8A-D, container tub 530 is shown located in fiducial locating opening 132, which is obscured by tub 530 while tub 530 is having its cover 520 removed or peeled by cover removal station 140. The use of engagement tool 142 and cover removal fixture 540 attached to cover 520 has already been described.

Figure 7:
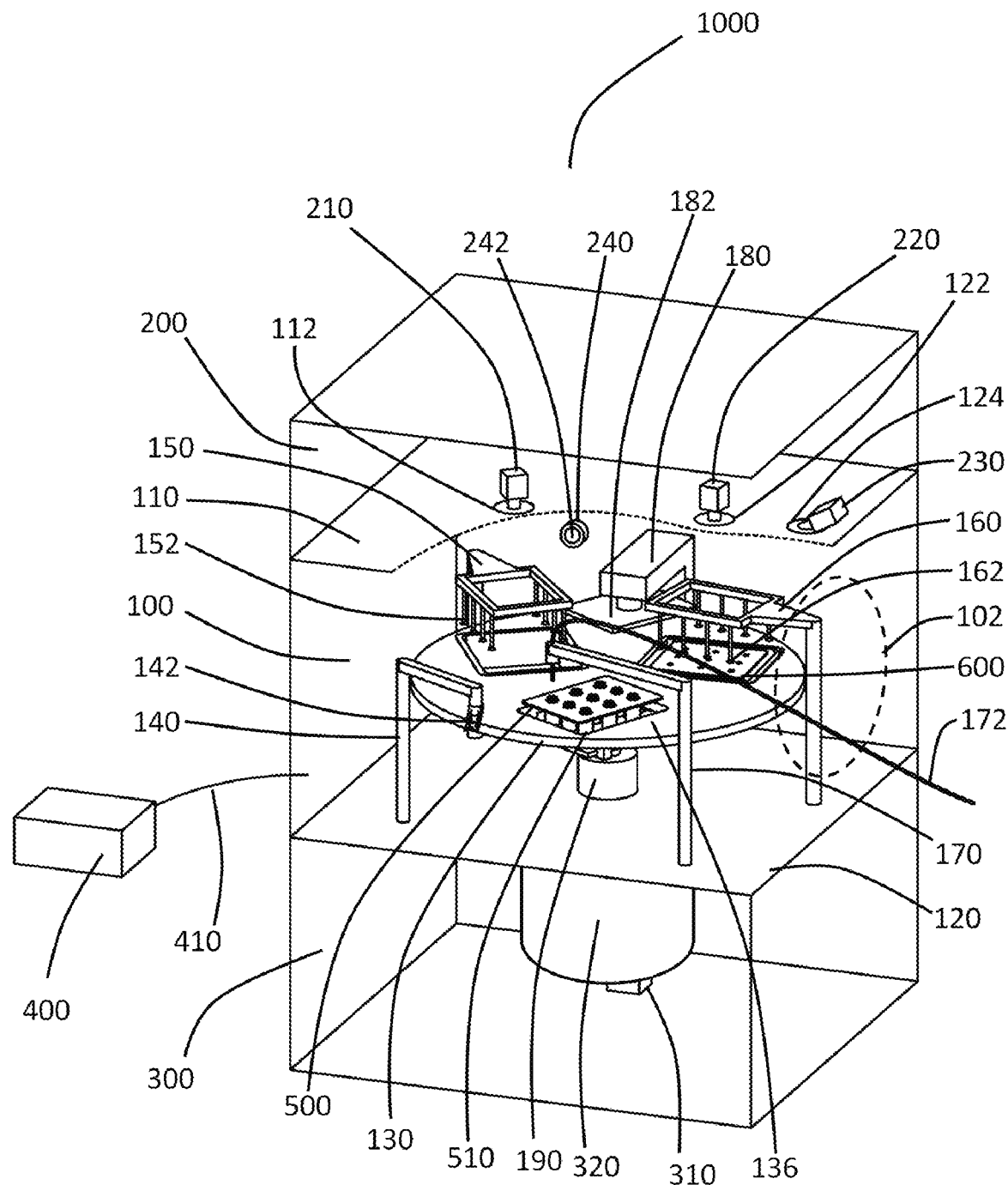
FIG. 7 is a drawing of the apparatus of FIG. 1A-G additionally equipped with a light source and a further sensor.

As shown in FIG. 7, filling system 1000 may comprise peeling monitor light source 240 disposed to illuminate a portion of rotary stage 130 proximate cover removal station 140. Peeling monitor light source 240 provides a suitably high amount of illumination to ensure that its illumination dominates strongly over any ambient light in system 1000. In order to further ensure that the illumination from light source 240 may be differentiated from ambient light, light source 240 may be of a selected wavelength or wavelength range. One suitable choice of device for light source 240 may be an infrared light emitting diode. Light source 240 may be provided with optical wavelength filter 242 that transmits only light of suitably differentiated infrared radiation. Light source 240 may illuminate the relevant portion of rotary stage 130 through sealed window separating light source 240 from sealable chamber 100. For the sake of clarity, sealed window separating light source 240 from sealable chamber 100 is not shown in FIG. 7.

Since suitable contrast is advantageous in monitoring the cover removal or the "peeling" process, and since rotary stage 130 may have a surface exhibiting an amount of reflectivity that may interfere with the working of peeling monitor sensor 230, light source 240 and peeling monitor sensor 230 maybe disposed relative to each other in such fashion as to ensure that light from light source 240 that is directly reflected by rotary stage 130 is not directed toward peeling monitor sensor 230. To this end, peeling monitor sensor 230 may be disposed facing the portion of rotary stage 130 proximate cover removal station 140, but located at a position that is outside any plane defined by any line perpendicular to rotary stage 130 within the area of rotary stage 130 illuminated by source 240 and the path of any light from light source 240 to the point where the perpendicular line intersects the illuminated surface of rotary stage 130. However, it is also advantageous for peeling monitor sensor 230 to have as near to a plan view of the illuminated area of rotary stage 130 as possible, without suffering direct reflection from rotary stage 130.

In FIG. 7, an example placement of peeling monitor sensor 230 and light source 240 is given. The portion of rotary stage 130 proximate cover removal station 140 is illuminated by light source 240 at a slanting angle, with light source 240 disposed in the back wall of sealable chamber 100 in order to achieve the required angle. Peeling monitor sensor 230 is disposed in upper wall 110 of sealable chamber 100. As is readily evident from FIG. 7, light from light source 240 will not be specularly reflected by the surface of the portion of rotary stage 130 proximate cover removal station 140. This allows light from light source 240 diffusely reflected by cover 520 of tub 530, when being removed from tub 530 by cover removal station 140, to dominate in the light received by peeling monitor sensor 230.

We turn now to FIGS. 8A-D representing a progression of stages in the removal of cover 520 from tub 530 by cover removal station 140. In the present specification, the phrase "monitored area" is used to describe area 232 of FIGS. 8A-D that is illuminated by light source 240 and monitored by peeling monitor sensor 230. During the peeling or removal of cover 520 in system 1000, rotary stage 130 is rotated and therefore monitored area 232 changes position on rotary stage 130 in the process.

Other pharmaceutical filling systems may be arranged differently and may function differently as regards the location of fiducial locating openings for tubs. For example, in such other systems the fiducial locating openings may be stationary and the covers may be removed solely by manipulating an associated cover removal station. In yet further systems, the fiducial locating openings may be moved linearly, rather than being rotated as in the case of system 1000. In the broadest implementation of the monitoring and control system for cover removal from tubs bearing pharmaceutical containers or closures, we concern ourselves only with the fact that the cover is somehow peeled from the tub it is attached to.

In FIGS. 8A-D, tub 530 has a substantially rectangular shape with four corners and entire tub 530 is tightly sealed against the environment by cover 520 when tub 530 is initially placed in fiducial locating opening 132, which is obscured by tub 530 in FIGS. 8A-D. Cover 520 has four corresponding corners. The first corner of cover 520 to be peeled from tub 530 is the corner that is shown furthest from cover removal station 140 in FIG. 8A. In one implementation of the cover removal monitoring and control system of the present specification the peeling of the first corner of the cover is not monitored.

Figure 8A:
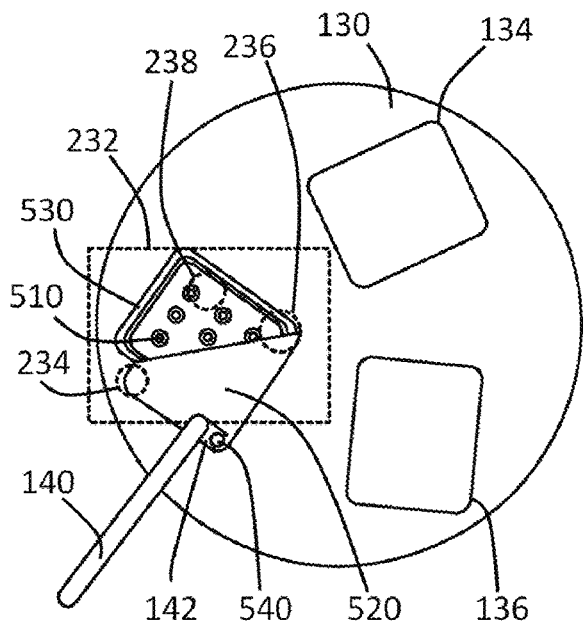
FIG. 8A-D is a set of drawings showing the peeling in the system of FIG. 7 of a cover from a tub sealed by the cover along with the use of the light source and further sensor to monitor and control the peeling of the cover.

FIG. 8A shows the situation very shortly after the peeling of the next corner of cover 520, being in this embodiment the corner of cover 520 corresponding to the leftmost corner of tub 530 in FIG. 8A. In the case of system 1000, the peeling of the first and second corners of cover 520 is by rotation of rotary stage 130 while the first corner of cover 520 is held by cover removal station 140 using engagement tool 142 and cover removal fixture 540, as described above in the present specification.

By suitable choice of the exact location of a first peeling monitor zone 234 within monitored area 232, proximate the second corner of tub 530 and substantially non-overlapping with container tub 530 immediately upon completion of the peeling of cover 520 from the second corner of tub 530, the light signal or image brightness produced by sensor 230 when the second corner of cover 520 has been peeled may be made to be very large, allowing thereby a sensitive measure of whether or not the second corner has been successfully peeled. This results from generally white cover 520 substantially covering monitor zone 234 at the moment of peeling being completed and diffusely reflecting light from light source 240 in the direction of peeling monitor sensor 230.

The term "peeling monitor zone" is used in this specification to describe a range of positions that the system is configured to evaluate in determining peeling status. This may be an entire three-dimensional volume having a base defined by, for example, dotted line 232 in FIG. 8A and an apex defined by sensor 230, making peeling monitor zone 234 an oblique cone. To the extent that cover 520, upon being peeled, intrudes into this oblique cone, cover 520 is overlapping into peeling monitor zone 230. A variety of other suitable zone dimensions may also be provided, such as a collimated cylindrical zone, a narrowly focused beam, or even a moving scanned beam. It is also to be noted that, in general, the base of the three-dimensional volume constituting the peeling monitor zone does not have to be restricted to a single plane, nor does it have to have a base that is a conic section. The base may be a defined portion of a field of view of sensor 230, and may be distributed over different physical surfaces within filling system 1000. It may also be possible to restrict how far the detection zone extends above the base.

The capture of the signal or image from sensor 230 may be timed to coincide with the moment that peeling of the second corner is completed. If sensor 230 is an imaging sensor, monitor zone 234 may be software-selected within the image produced by sensor 230. If sensor 230 is non-imaging sensor, then a simple measurement of absolute light signal will serve the same purpose. In both implementations, the distinction between unpeeled and peeled may be made on the basis of the total light signal received from first corner peeling monitor zone 234. To differentiate a good peel from a bad peel, a "floor value" may be set for the absolute signal measured by sensor 230 from monitor zone 234. If sensor 230 is an imaging sensor, then the measurements may be, for example without limitation, an average over the image received from monitor zone 234. It is to be noted that the method requires no extensive image management or perspective correction, nor any compensation for lens distortions and the like, as are often required in machine vision applications. And while it is presently contemplated that the method would be performed in connection with software running on controller 400 or other processor, it may be implemented at least in part with dedicated hardware.

Figure 8B:
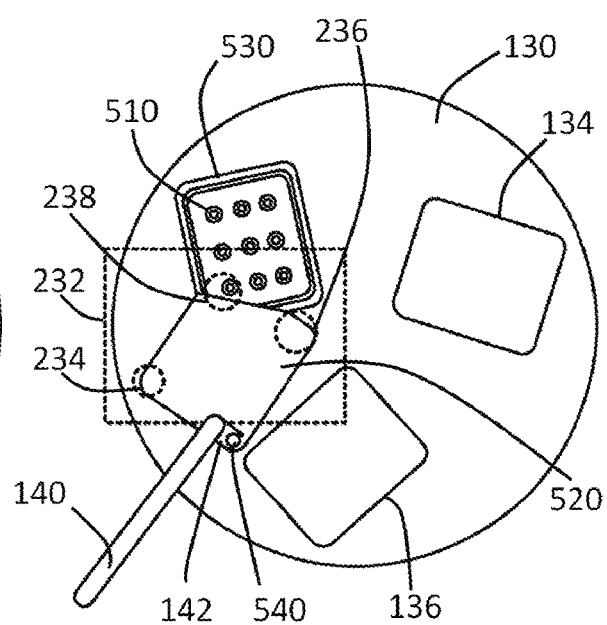

In FIG. 8B the peeling of a third corner of cover 520 is shown, being the right-most corner of cover 520 in FIG. 8A. In FIG. 8B, rotary stage 130 has been rotated a number of degrees clockwise with respect to FIG. 8A so as to peel the third corner of cover 520, which is shown in FIG. 8B as having been peeled. As is the case with the second corner of cover 520, by suitable choice of the exact location of peeling monitor zone 236, proximate the third corner of tub 530 and substantially non-overlapping with container tub 530 immediately upon completion of the peeling of cover 520 from the third corner of tub 530, the diffusely reflected signal or image produced by sensor 230 when the third corner of cover 520 has been peeled may be caused to be very large, allowing thereby a sensitive measure of whether or not the third corner has been successfully peeled. The method for determining the quality of the peeling of the third corner may proceed exactly as is the case with the second corner, with the exception that it is light reflected from peeling monitor zone 236 that is used to make the determination. In the case of system 1000, the peeling of the first, second, and third corners of cover 520 is by rotation of rotary stage 130 while the first corner of cover 520 is held by cover removal station 140 using engagement tool 142 and cover removal fixture 540, as described above in the present specification.

Figure 8C:
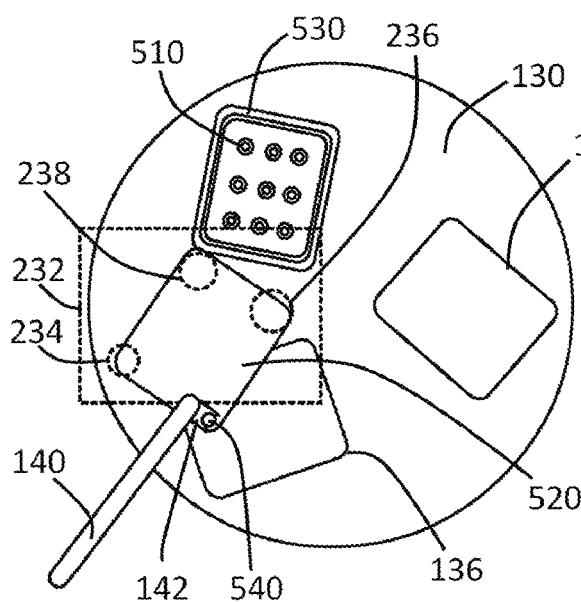
Figure 8D:
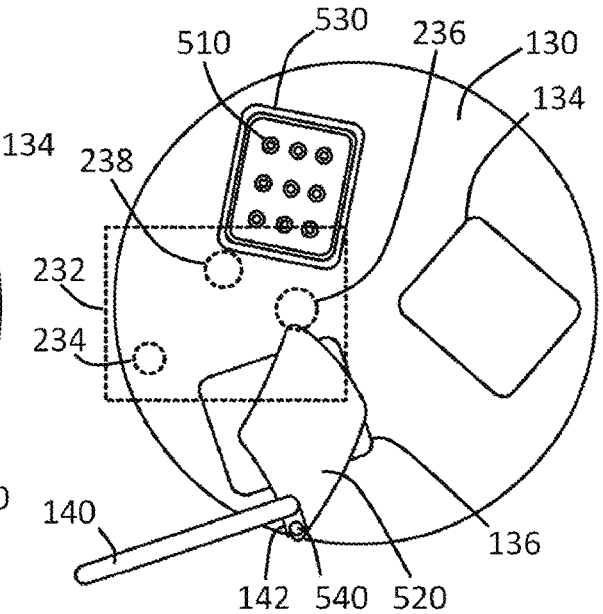

The peeling of the fourth and last corner of cover 520, as per FIGS. 8C and D, presents somewhat of a different challenge. Unlike the second and third corners, the quality of the peel cannot be assessed solely on the basis of the white diffusely reflecting cover 520 covering any peeling monitor zone proximate tub 530, because that would actually be evidence of the peeling having not been completed. A slightly different approach is therefore followed. Again a suitable peeling monitor zone is chosen, being zone 238 proximate the fourth corner of tub 530 and substantially non-overlapping with tub 530 immediately upon completion of the peeling of cover 520 from the fourth corner of tub 530. Two measurements are made of zone 238, namely, a measurement at the time of FIG. 8C just before cover 520 finally detaches from tub 530, and another as per FIG. 8D after it has been detached by the rotation of cover removal station 140. The first of the two measurements should have a high signal as a result of cover 540 diffusely reflecting a lot of light from light source 240 in the direction of peeling monitor sensor 230, and the second measurement should be very low, due to the absence of any white diffusely reflecting cover material of cover 520 in zone 238. In a general implementation of the monitoring and control system for cover removal from tubs bearing pharmaceutical containers or closures, rotary stage 130 and cover removal station 140 may be moved sequentially or may be moved simultaneously.

Figure 9:
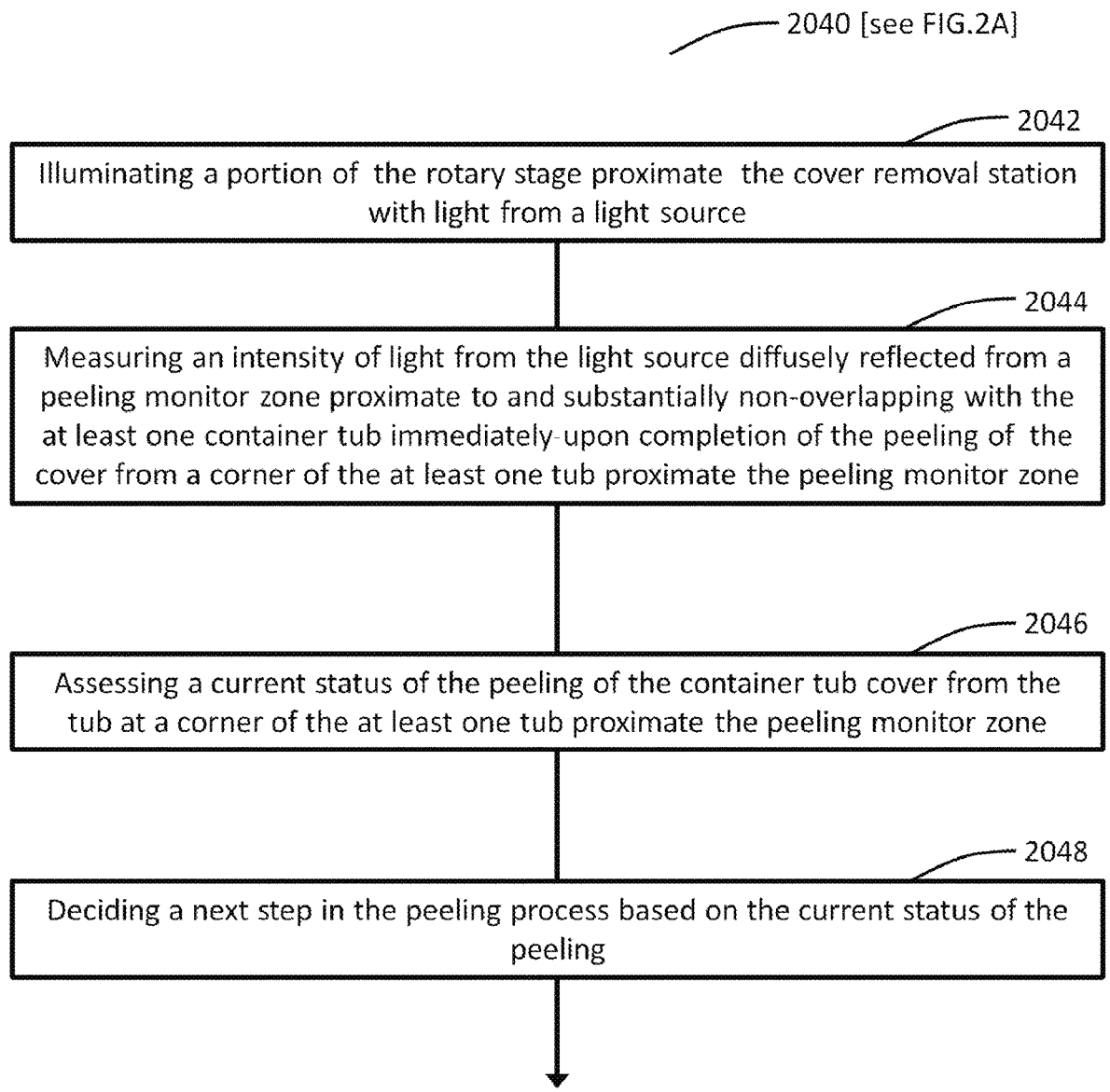
FIG. 9 shows a flow chart providing more detail of the peeling step of the flow chart in FIG. 2A as performed using the system of FIG. 7 and FIG. 8A-D.

Based on the above description, the method for aseptically filling pharmaceutical containers with a pharmaceutical fluid substance described above at the hand of the flow chart of FIG. 2A may further comprise as per the flow chart in FIG. 9: monitoring and controlling removing [2040] container tub cover 520 from the at least one container tub 530 by a method comprising: illuminating [2042] portion 232 of rotary stage 130 proximate cover removal station 140 with light from light source 240; measuring [2044] an intensity of light from light source 240 diffusely reflected from peeling monitor zone 234, 236, 238 proximate to and substantially non-overlapping with the at least one container tub 530 immediately upon completion of the peeling of cover 520 from a corner of the at least one tub 530 proximate peeling monitor zone 234, 236, 238; assessing [2046] a current status of the peeling of container tub cover 520 from the at least one tub 530 at a corner of tub 530 proximate peeling monitor zone 234, 236, 238; deciding [2048] a next step in the peeling process based on the current status of the peeling.

In the above description of the peeling process, the peeling monitor zones have been chosen to be proximate the relevant corner being peeled and substantially non-overlapping with tub 530 and the measurements of reflected light are done immediately upon completion of the peeling of cover 520 from the relevant corners of tub 530. It will be understood that in some embodiments the measurements may be done at predetermined times after completion of the peelings of the corresponding corners, and the corresponding peeling monitor zones may be chosen to be at commensurately different corresponding locations proximate the corresponding corners of tub 530 and substantially non-overlapping with tub 530, and still in the illuminated portion of stage 130.

In some embodiments, instead of single peeling monitor sensor 230 being employed, a plurality of separate peeling monitor sensors may be employed with a different one of the plurality of sensors dedicated to measuring the light reflected from each individual peeling monitor zone, for example peeling monitor zones 234, 236, and 238. In further embodiments, a plurality of light sources may be employed, allowing a separate light source to serve as illumination for each corresponding corner of tub 530 to be monitored for peeling. In yet further embodiments, different wavelengths of illumination may be employed for the different corners to be monitored and the sources and sensors matched accordingly by wavelength or wavelength range.

The output of sensor 230 may be used in a variety of ways. In one embodiment, the sensor may provide via software in controller 400 a signal that indicates whether a corner has been successfully peeled. If this signal indicates successful peeling of one corner, the controller may cause the system to continue peeling the cover until the next sensing step is performed, and this process may continue until the cover is completely removed. If the sensor detects a failure to remove a corner, the controller may stop the movement of the platform, issue an alert, and/or provide another action that will allow the condition to be inspected and/or remedied.

Assessing [2045] may comprise comparing the intensity of light from measuring [2044] with a predetermined light intensity value. The predetermined light intensity value may be chosen such that, if it is exceeded by the measured light intensity during measuring [2044], it represents a large presence of tub cover 520 within peeling monitor zone 234, 236, 238, which in turn is evidence of tub cover 520 having been successfully removed from the corner of tub 530 proximate peeling monitor zone 234, 236, 238. Illuminating [2042] with light from light source 240 may be illuminating [2042] with infrared light from light source 240.

The predetermined light intensity value may be stored in the memory of controller 400. Controller 400 may contain suitable software programming instructions which, when loaded in the memory and executed by the processor, control the rotating action of rotary stage 130, measurements by sensor 230, and any rotational or vertical motions required from cover removal station 140 in mutually dependent and synchronized fashion. This allows measuring [2044] to be timed to take place immediately upon completion of the peeling of the cover 520 from a corner of the at least one tub 530 proximate peeling monitor zone 234, 236, 238. The second measurement associated with the fourth corner of tub 530 may similarly be timed to take place when tub cover 520 has been completely detached from tub 530. An assessment of the peeling of the last corner of tub 530 is made based on the last measurement returning a light intensity that is lower than a predetermined value associated with peeling monitor zone 238. The sequence of high diffusely reflected light intensity followed by low diffusely reflected light intensity is evidence of the peeling at the last corner respectively taking place and cover 520 having been completely detached and removed from peeling monitor zone 238. By the above approach the cover removal monitoring and control process may be completely automated.

The same cover removal station 140, light source 240, sensor 230, and peeling monitor zones 234, 236, 238 may be employed to also remove a cover from a container closure tub by the same method as described above.

Though the apparatus and method for monitoring the removal of a cover from a tub has been described above at the hand of a system employing a rotary turntable comprising a simple fiducial locating opening for holding the tub in a predetermined fixed position, this represents but one non-limiting example of a suitable system comprising a platform having a fiducial source locating structure. In general, the platform is not limited to being a rotary stage. The platform may be a movable platform and may be movable through any general path that allows removal of the cover by a suitable cover removal station. The source fiducial locating structure may be any fiducial locating structure that is capable of holding the tub in a predetermined fixed position, including those described at the hand of FIGS. 3A, 3B, 4A, and 5A.

In one example, the system may be adapted to monitor cover removal in an apparatus of the type described in above-referenced United States Patent Application Publications US 2017-0248626 and US 2016-0251206, which employs an articulated arm to hold the tub during cover removal. Since there is no rotary stage 130 in this case, monitored zone 232 will extend over another peeling monitor surface inside the aseptic chamber, such as a top surface of a pedestal. And while it is presently preferred that the surface be a horizontal surface that is monitored from the top, it may also be possible in some instances to monitor the cover removal process from another vantage point, such as from the bottom up. The optical properties of the monitored zone or at least peeling monitor zones 234, 236, 238 may be provided with suitable optical properties to enhance the monitoring process. This may be achieved in a variety of ways, such as by the selection of the material that defines the monitored zone or by applying a coating or other surface treatment to some or all of the monitored zone.

The system may also be reorganized in a variety of ways. Instead of the top-down reflective measurement presented above, for example, a bottom-up transmissive measurement may be performed by placing one or more light sources at one or more peeling detection zones in the in the monitored zone, such as by embedding them in the platform. The system would then detect successful peeling by looking for the cover to block light from the light sources from reaching the sensor.

Figure 3A:
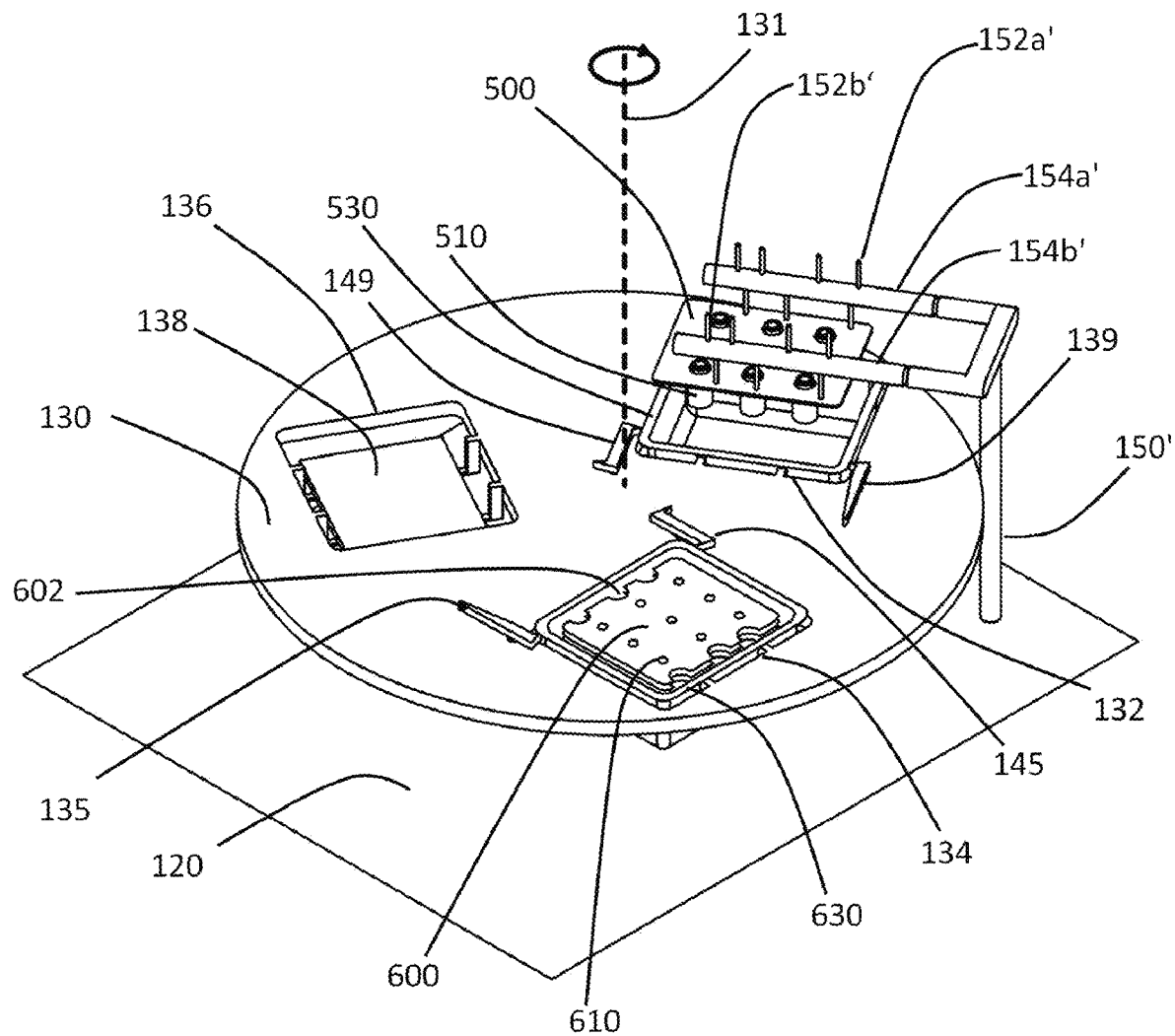
FIG. 3A is a drawing of subsystems of another embodiment of an apparatus for filling pharmaceutical containers with a pharmaceutical fluid product.
Figure 3B:
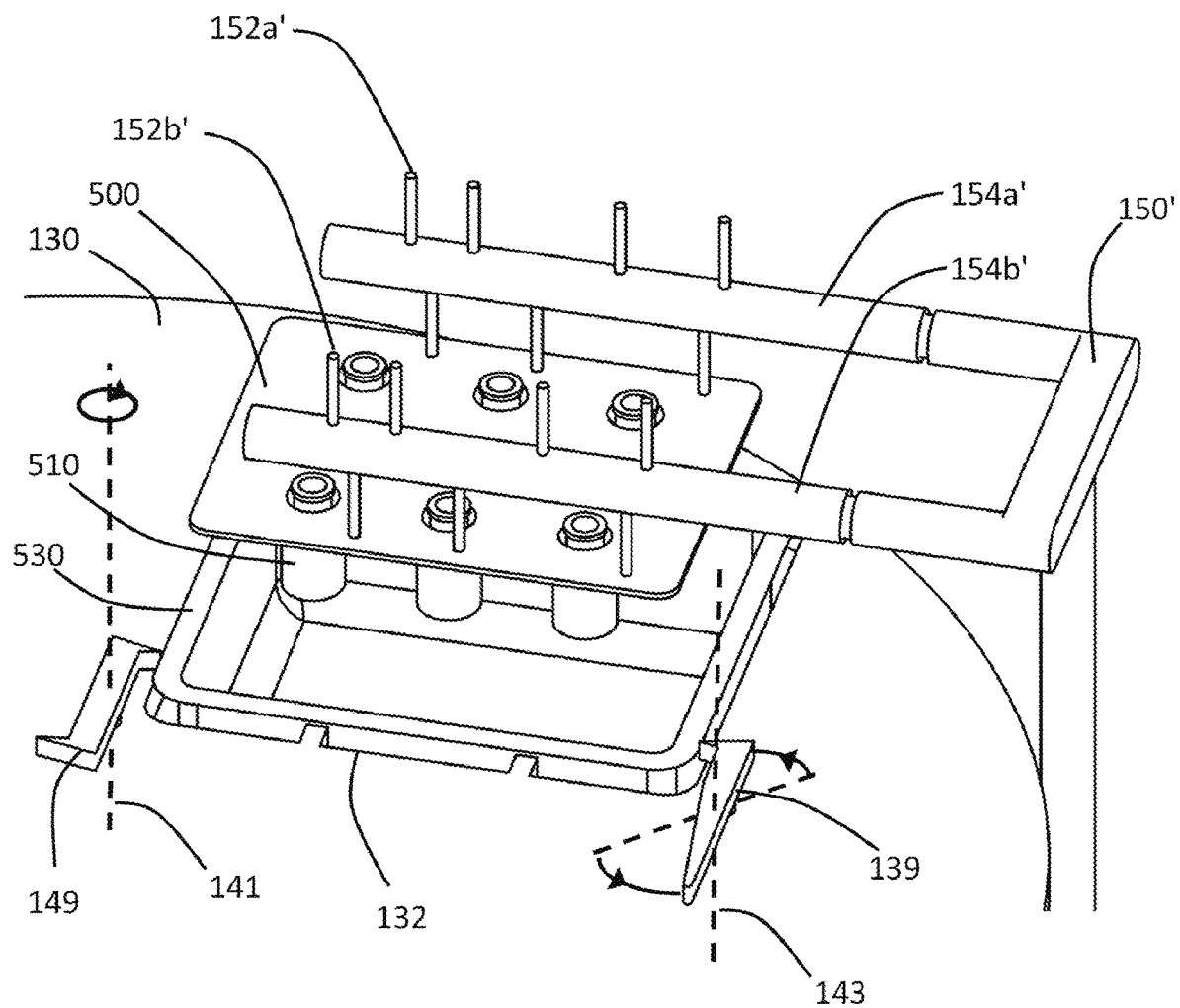
FIG. 3B shows a portion of FIG. 3A in more detail.

Another embodiment of a filling system according to the invention may be in all respects identical to the embodiments described above at the hand of FIGS. 1A and 1B, with the exception of vacuum pickup system(s) 150 or 160. FIGS. 3A and 3B show a portion of a filling system as described above. FIG. 3B, in particular, focuses on the general area of one of the vacuum pickup systems, by way of example, vacuum pickup system 150. In this alternative embodiment, vacuum pickup system 150 is replaced by reconfigurable vacuum pickup system 150'. Vacuum pickup system 160 of FIGS. 1A and 1B may similarly be replaced by reconfigurable vacuum pickup system 160' of the same arrangement as vacuum pickup system 150'. In the interest of clarity, vacuum pickup system 160' is not shown in FIG. 3A or 3B. In other embodiments, a single reconfigurable vacuum pickup system 150' may be employed to pick up both container nests and container closure nests. Vacuum pickup system 150' may access the container nests and container closure nests by rotation of rotary stage 130.

Vacuum pickup system 150' comprises two rotary arms 154a' and 154b', in their turn respectively comprising pluralities of suction cups 152a' and 152b'. Vacuum pickup system 150' is arranged to pick up nests 500 of containers 510 by means of suction cups 152a' and 152b'. Vacuum pickup system 150' may also be arranged to pick up nests 600 of container closures 610 by means of suction cups 152a' and 152b'. As with vacuum pickup system 150, vacuum pickup system 150' may be raised and lowered in order to allow suction cups 152a' and 152b' to engage with different nests 600 of container closures 610 contained at differing depths inside tub 630.

Suction cups 152a' and 152b' are arranged on rotary arms 154a' and 154b' as pluralities of sets of linearly arranged suction cups 152a' and 152b', each set of linearly arranged suction cups 152a' and 152b' being arranged at a different angle perpendicular to the longitudinal axes of rotary arms 154a' and 154b'. This arrangement allows rotary arms 154a' and 154b' to be rotated about their longitudinal axes in order to orient different sets of linearly arranged suction cups 152a' and 152b' to engage with different nests 500 of containers 510. This allows the sets of suction cups 152a' and 152b' to be individually selectable for use. Rotation of rotary arms 154a' and 154b' may be performed manually. In other embodiments, rotation of rotary arms 154a' and 154b' may be by means of a suitable motorized drive incorporated in vacuum pickup system 150' and controlled by controller 400 shown in FIG. 1A.

By selecting different sets of linearly arranged suction cups 152a' and 152b' via the rotation of rotary arms 154a' and 154b', the sets of suction cups 152a' and 152b' may be disposed to engage with different container nests 500 bearing containers 510, or container closure nests 600 bearing container closures 610.

FIGS. 3A and 3B show vacuum pickup system 150' as comprising two rotary arms, being rotary arms 154a' and 154b'. In other embodiments, one or more arms may be employed, all embodiments sharing the concept of a selectable configuration of suction cups. Whereas the selection of suction cup configurations in FIG. 3A and FIG. 3B is by means of rotation of the arms 154a' and 154b' bearing the suction cups 152a' and 152b', the selecting in other embodiments may be on a different basis of configuration, including, for example without limitation, lateral translation of suction-cup-bearing arms in a plane parallel to the rotation plane of rotary stage 130 in order to engage different sets of suction cups with container nests or container closure nests. In FIGS. 3A and 3B suction cups are arranged in linear sets. In other embodiments non-linear arrangements of suction cups may be employed.

Turning now to FIG. 3B specifically, we consider members 149 and 139 in more detail. In one embodiment, reconfigurable stopping member 149 is shown as having two different ends of which a first end may be selected for use by suitable rotation of reconfigurable stopping member 149 about stopping member rotation axis 141 to a predetermined set position. In the set position, reconfigurable stopping member 149 provides a hard stop for a proximal end of container 530 against the selected end of reconfigurable stopping member 149 along a direction parallel to the longitudinal axes of rotary arms 154a' and 154b'. In this embodiment, reconfigurable stopping member 149 may be rotated through 180 degrees to dispose the second end of reconfigurable stopping member 149 to stop container 530. The second end of reconfigurable stopping member 149 may be configured to stop the proximal end of container 530 at a different point than where the first end of reconfigurable stopping member 149 stops the proximal end of container 530.

Restraining member 139 is configured to push against a distal end of container 530. While different mechanisms are contemplated to ensure the pushing action of restraining member 139, one particular suitable means is by providing restraining member 139 with suitable spring loading to rotate about axis 143. By the above operation, reconfigurable stopping member 149 and restraining member 139 together allow container 530 to be positioned at an exact location parallel to the longitudinal axes of rotary arms 154a' and 154b'. The particular exact location is selectable by selecting the appropriate end of reconfigurable stopping member 149 to stop container 530. This arrangement allows containers 530 of different dimensions parallel to the longitudinal axes of rotary arms 154a' and 154b' to be located at exact predetermined locations with respect to sets of suction cups 152a' and 152b'.

A particular set of suction cups 152a' and 152b' may be selected to match the selection of the particular end of reconfigurable stopping member 149. In this way, vacuum pickup system 150' may be set to a configuration that ensures that a selected size of container 530 is precisely positioned to allow container nests 500 within container 530 to be engaged by specific sets of suction cups 152a' and 152b'. Vacuum pickup system 150' is thereby reconfigurable to engage with nests of different sizes within containers of different sizes.

In the interest of clarity, the description above, as well as FIGS. 3A and 3B, show an arrangement that allows for the exact positioning of containers 530 along only one dimension in the rotation plane of rotary stage 130, the dimension of the containers perpendicular to the one dimension being assumed to be identical. In such an arrangement, fiducial locating openings 132 and 134 are sized to constrain containers 530 in the perpendicular dimension in the rotation plane of rotary stage 130.

In another embodiment, a further reconfigurable stopping member and restraining member may be added to the arrangement of FIG. 3A and FIG. 3B in order to address the positioning of container 530 in the perpendicular direction within the rotation plane of rotary stage 130. To allow the positioning of container 530 in this perpendicular direction, fiducial locating openings 132 and 134 are not sized to constrain containers in any direction within the rotation plane of rotary stage 130.

In the embodiments described above, reconfigurable stopping member 149 has been described as having two ends of which one is selected for use at any one time by rotating reconfigurable stopping member 149 about stopping member rotation axis 141. In other embodiments, reconfigurable stopping member 149 may be shaped or configured to have more than two stopping ends, the ends being selectable by suitable rotation of reconfigurable stopping member 149 about stopping member rotation axis 141. In one embodiment, in which the reconfigurable stopping member has a very large number of stopping ends, the reconfigurable stopping member may assume the shape of a cam, representing a large plurality of possible stopping ends that may be selected via rotation of the reconfigurable stopping member about a suitable stopping member rotation axis.

In general, the system described at the hand of FIGS. 3A and 3B comprises a reconfigurable fiducial nest positioning system. The reconfigurable fiducial nest positioning system comprises a movable platform comprising fiducial locating opening 132, reconfigurable stopping member 149, and restraining member 139. In the case of the system of FIGS. 3A and 3B, the movable platform is rotary stage 130. As explained later, other movable platforms are also contemplated. To the extent that, for example, tub 530 positionally constrains and locates nest 500 inside tub 530, any system that fiducially locates tub 530 inherently also fiducially locates nest 500.

The various embodiments contemplated all comprise a reconfigurable vacuum pickup system that may be configured to engage its suction cups with corresponding areas on a pharmaceutical container nest. The containers in the container nest may be closed by corresponding container closures suspended in a container closure nest. The planar surface of the container closure nest may have an outline that leaves pass-throughs on its perimeter for the suction cups to pass through to engage with the container nest. By way of example, in FIG. 3a pass-throughs 602 are shown on the perimeter of closure nest 600. Alternatively or additionally, the container closure nest may have suitable openings in its planar interior to serve as pass-throughs for the suction cups to pass through to engage with the container nest. The vacuum pickup systems contemplated are further configured and disposed to pick up the combination of nested containers and their closures by the container nest, as opposed to by the closure nest.

In a general embodiment, a nest handling subsystem comprises a reconfigurable vacuum pickup system for picking up container nests and/or container closure nests may comprise one or more arms bearing a plurality of sets of suction cups. By reconfiguration of the vacuum pickup system a set of suction cups may be selected from among the plurality of sets of suction cups, the selected set of suction cups being pre-arranged to engage with a particular container nest or container closure nest. The selection may be on the basis of one or both of the size and the shape of the nest. The nest handling system may further comprise at least one pair of reconfigurable stopping members 149 and restraining member 139 disposed proximate opposing ends of fiducial locating opening 132 for holding tub 530 containing container nests 500 bearing containers 510 in order to engage with opposing ends of tub 530. The stopping and restraining members are disposed to position tub 530 in a predetermined position that ensures that the selected set of suction cups may engage with the container nests and/or container closure nests.

As is the case with opening 132, opening 134 of FIG. 3A may also be served by at least one set of a reconfigurable stopping member, being member 145 in this case, and a restraining member, being member 135 in this case. Reconfigurable stopping member 145 and restraining member 135 function with respect any tub in opening 134 in the same way as reconfigurable stopping member 149 and restraining member 139 function with respect any tub in opening 132.

The various embodiments above have been described in terms of FIG. 1A to E and FIG. 3A, and FIG. 3B in which the vacuum pickup system 150, 160 is described as part of pharmaceutical filling system 1000. However, vacuum pickup system 150', 160' may also be employed in its own right other apparatus not limited to the filling system of FIG. 1A to 1E, or, in fact, to filling systems in general. Some other example applications include, without limitation, lyophilizing systems. It may be applied to suitable nests of any objects arranged in a predetermined pattern. Furthermore, while the system 1000 of FIG. 1A to FIG. 1E employs rotary stage 130, reconfigurable vacuum pickup system 150' may employ any suitable movable platform comprising suitable fiducial locating openings.

The method described above at the hand of FIGS. 2A and 2B may now also be described in more detail with reference to FIG. 3A and FIG. 3B. The providing at least one vacuum pickup system as part of the providing a filling apparatus step [2010] may comprise providing at least one reconfigurable vacuum pickup system 150', the at least one reconfigurable vacuum pickup system 150' comprising a plurality of sets of suction cups 152a' and 152b'.

The providing a filling apparatus step [2010] may comprise providing rotary stage 130 with destination fiducial locating opening 136 and at least two source fiducial locating openings 132, 134, each source fiducial opening having at least one pair of reconfigurable stopping members 149 and a restraining member 139.

The transferring step [2020] may comprise operating at least first reconfigurable stopping member 149 to stop container tub 530 at a predetermined container tub position and operating at least first restraining member 139 to restrain container tub 530 at the predetermined container tub position.

The transferring step [2025] may comprise operating at least second reconfigurable stopping member 145 to stop container closure tub 630 at a predetermined closure tub position and operating at least second restraining member 135 to restrain container tub 630 at the predetermined closure tub position.

The step of operating [2050] the at least one vacuum pickup system 150', 160' may comprise configuring the at least one reconfigurable vacuum pickup system 150', 160' to select a first predetermined set of suction cups disposed to engage with container nest 500.

The operating [2070] of one of the at least one vacuum pickup system 150', 160' may comprise configuring the at least one reconfigurable vacuum pickup system 150', 160' to select a second predetermined set of suction cups disposed for engaging with container closure nest 600.

The method may further comprise operating [2095] at least one vacuum pickup system 150', 160' with the first predetermined set of suction cups selected to engage with container nest 500 and jointly remove container nest 500 and container closure nest 600 from ramming system 180.

Figure 4A:
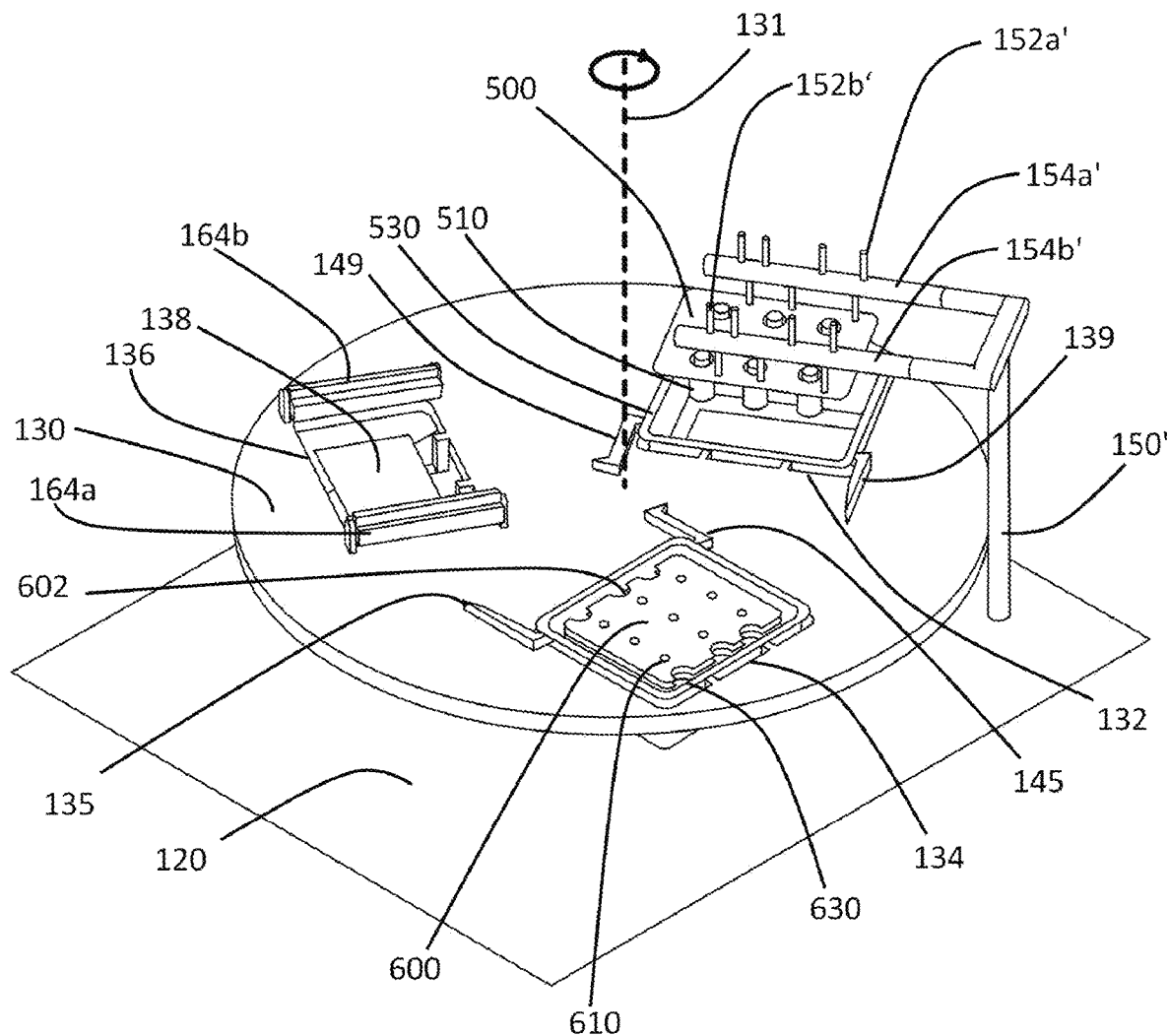
FIG. 4A is a drawing of subsystems of a further embodiment of an apparatus for filling pharmaceutical containers with a pharmaceutical fluid product.
Figure 4B:
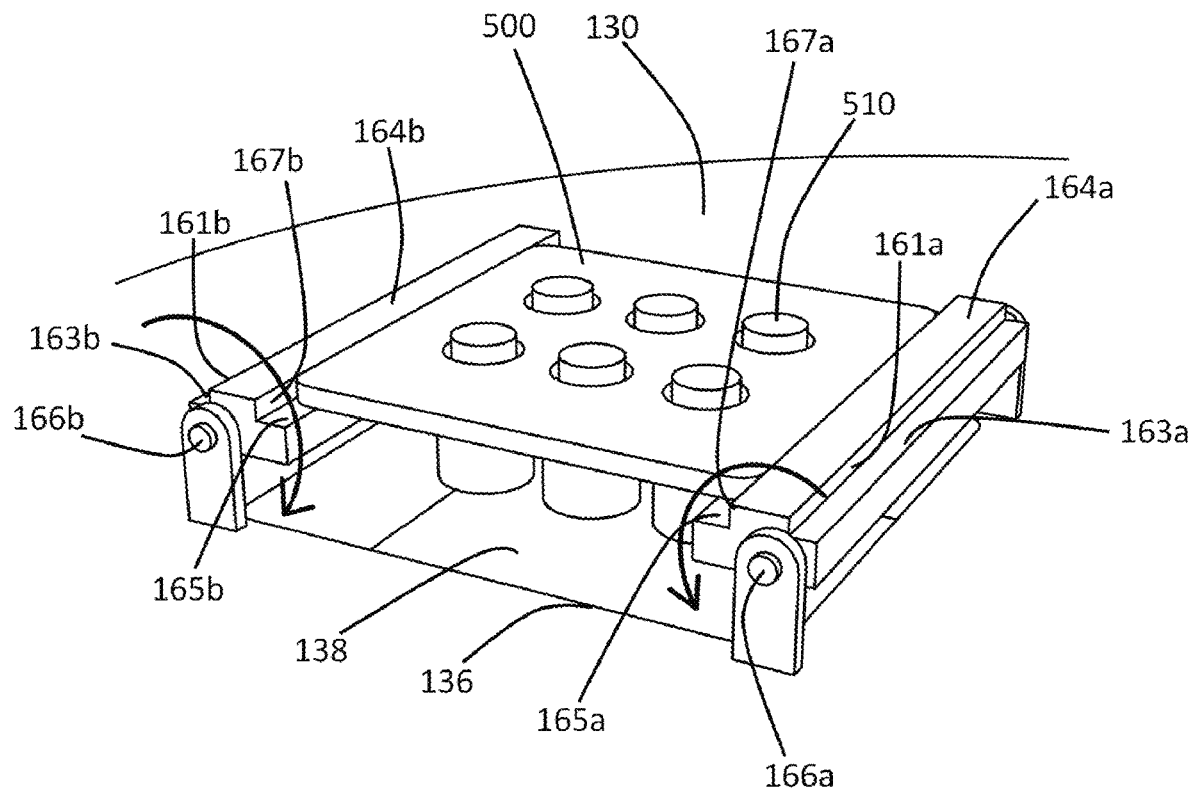
FIG. 4B shows a portion of FIG. 4A in more detail.

We have considered in FIG. 3A and FIG. 3B alternative embodiments of the arrangements of vacuum pickup systems 150 and 160 of FIG. 1a in the form of vacuum pickup systems 150' and 160'; and the positioning arrangements associated with source openings 132 and 134 in the form of elements 135, 145, 139, and 149. We now turn our attention to alternative embodiments for the arrangements around destination opening 136 of FIG. 1A and FIG. 3A. FIG. 4A and its close-up view in FIG. 4B show the system of FIG. 3A with a different embodiment of the arrangement around destination opening 136. While cameras 210 and 220 of FIG. 1A may be employed in conjunction with controller 400 and rotation of rotary stage 130 to position nest 500 at opening 136, and to position nest 600 over nest 500 at opening 136, the adjustable destination fiducial positioning system of FIG. 4A and FIG. 4B comprising rotary positioning elements 164a and 164b may be alternatively or additionally employed to accurately position nests 600 and 500.

Typical industrial container nests are not manufactured to a dimensional standard, and, as a result, any system for filling and closing nested containers 510 has to have a mechanism to accurately position differently sized nests 500 bearing containers 510. To this end, rotary positioning elements 164a and 164b may have different sets of paired positioning surfaces 167a,167b and 163a,163b allowing nests 500 of specific dimensions to be accurately fitted between such paired positioning surfaces. In FIG. 4B, nest 500 fits such that its two opposing ends in a first dimension touch mutually facing surfaces 167a and 167b of rotary positioning elements 164a and 164b respectively. By mutually counter-rotating elements 164a and 164b about respectively axes 166a and 166b, surfaces 167a and 167b may be made to face each other and may thereby allow the precise positioning between them of a nest of different length in the first dimension.

As is evident from FIG. 4B, when surfaces 167a and 167b face each other, the nest positioned snugly between them may be retained in a precise and predetermined vertical position by resting on surfaces 165a and 165b of rotary positioning elements 164a and 164b respectively. When surfaces 163a and 163b face each other, the alternative nest positioned snugly between them may retained in a precise and predetermined vertical position by resting on surfaces 161a and 161b of rotary positioning elements 164a and 164b respectively. Elements 164a and 164b may be rotated manually about axes 166a and 166b respectively. In some embodiments, the rotation of elements 164a and 164b may be done automatically by means of motorized drives controlled by controller 400 and suitable control software. That control may be based on predetermined dimensional data relating to the nest being positioned between the surfaces of elements 164a and 164b. It may also be based on input data derived from imaging data obtained from cameras 210 and/or 220. Further, the rotation may take place as nest 500 is lowered into position so that the particular surfaces of elements 164a and 164b destined to engage with the opposing ends of nest 500 along the first dimension may serve as closing horizontal grip on nest 500 as the surfaces rotate toward the position in which they face each other. In this embodiment, the horizontal positioning and vertical positioning of a nest between elements 164a and 164b are not mutually independent.

Another arrangement as shown in FIG. 4A and FIG. 4B for the first dimension of nest 500, may also be established for the second planar dimension of nest 500 perpendicular to the first dimension. This allows any nest 500 placed at opening 136 to be accurately located in a location predetermined by the choice of setting of rotary positioning elements 164a and 164b.

Figure 5A:
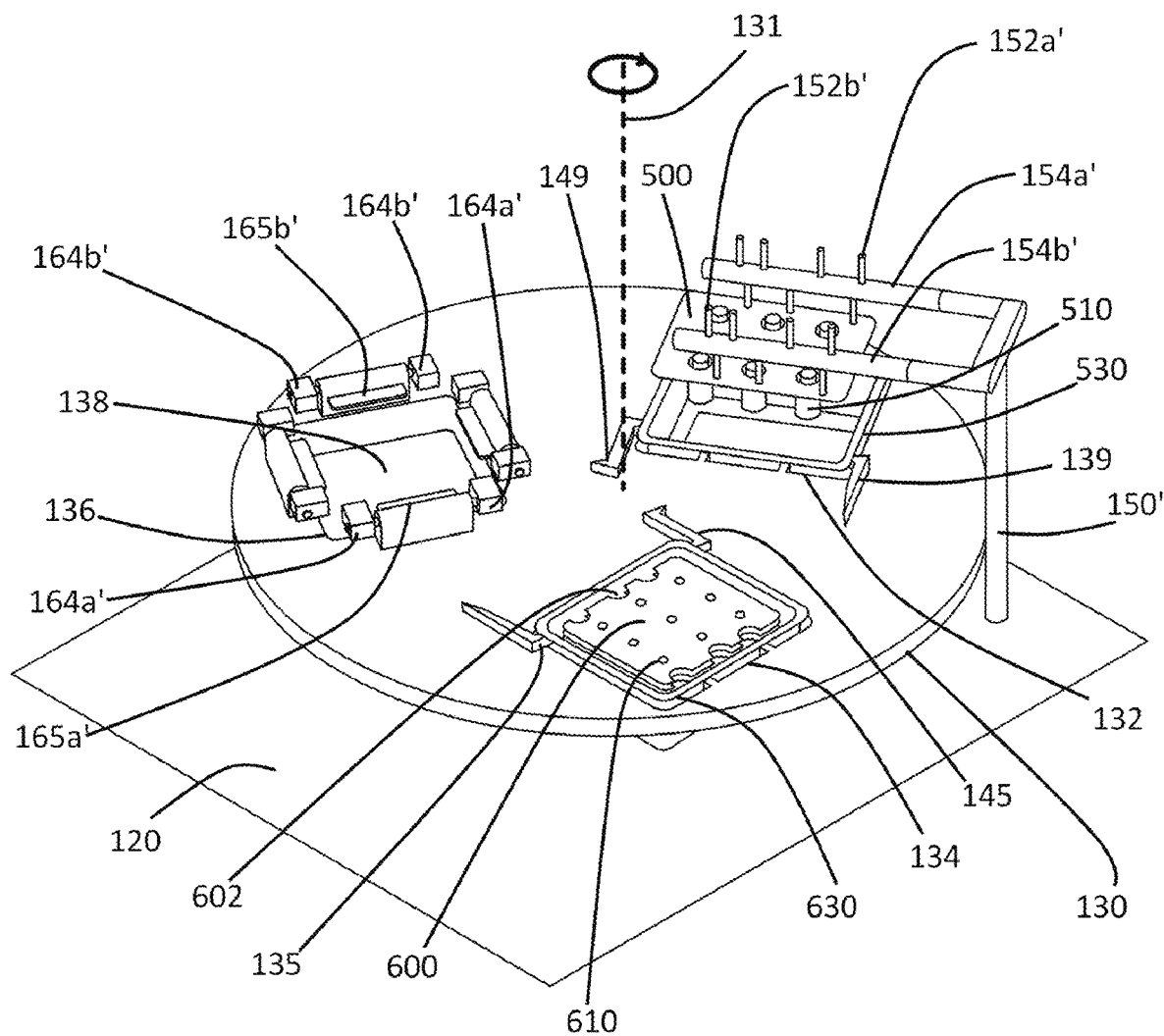
FIG. 5A is a drawing of subsystems of yet a further embodiment of an apparatus for filling pharmaceutical containers with a pharmaceutical fluid product.
Figure 5B:
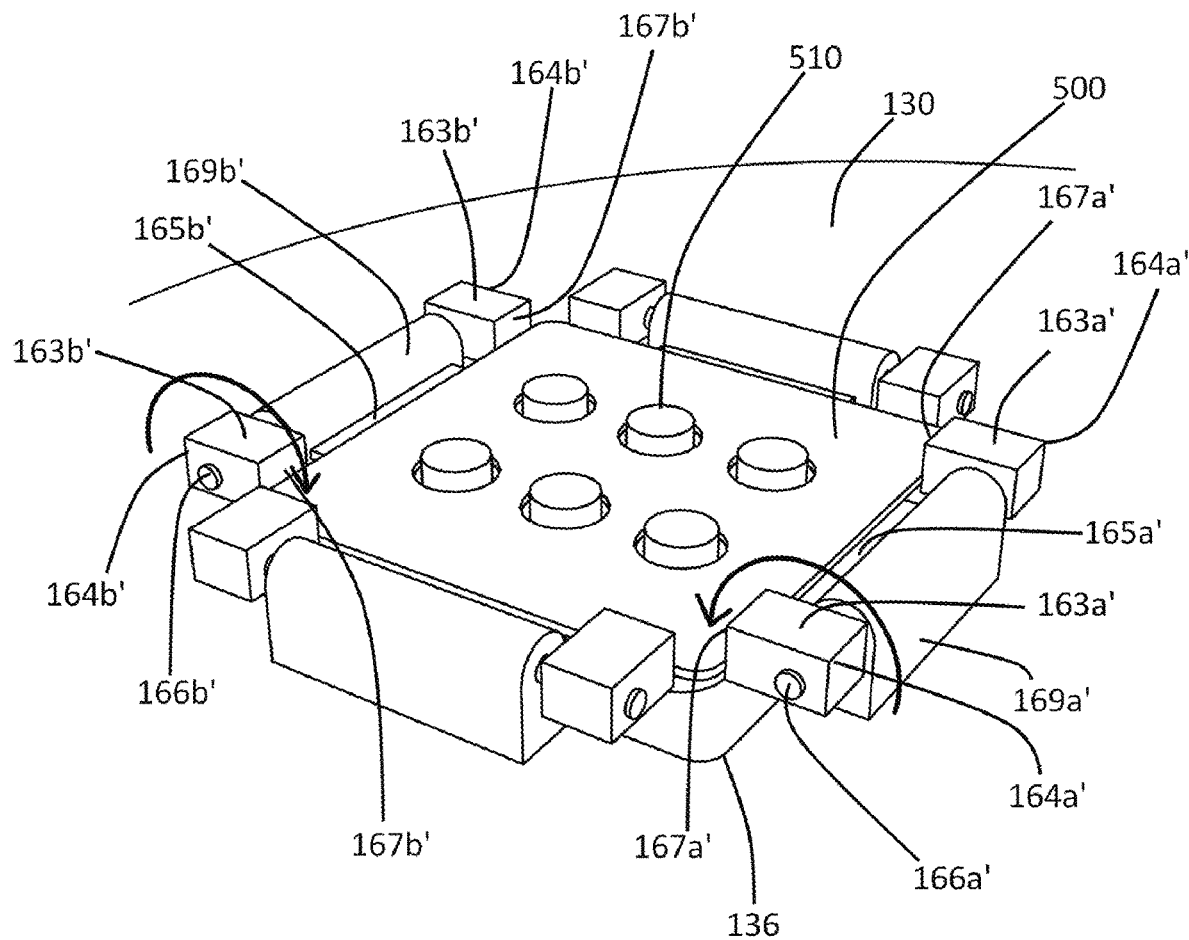
FIG. 5B shows a portion of FIG. 5A in more detail.

Another embodiment of rotary positioning elements is shown in FIG. 5A and FIG. 5B. In contrast with the embodiment of FIG. 4A and FIG. 4B described immediately above, the horizontal positioning and vertical positioning of a nest between two mutually counter-rotatable elements 164a' and 164b' in FIG. 5A and FIG. 5B are mutually independent positioning actions. This is achieved by employing, in each of the two mutually perpendicular planar dimensions addressed in the embodiment immediately above, a pair of fixed opposing planar tabs 165a' and 165b' to position nest 500 in the vertical dimension, and a pair of rotary positioning elements 164a' and 164b' to position nest 500 in the first horizontal dimension. In this embodiment, each of elements 164a' and 164b' comprise two rotatable elements ganged on axles 166a' and 166b' respectively to rotate in unison and mutual alignment either side of planar tabs 165a' and 165b' within bosses 169a' and 169b' respectively. The sets of rotary elements 164a' and 164b', beyond each being divided in to two ganged elements, serve to confine nest 500 in the horizontal dimension in the same fashion as rotary elements 164a and 164b in the embodiment of FIG. 4A and FIG. 4B described immediately above.

While elements 164a' and 164b' may be designed to be of more complex shape, we show in FIG. 5A and FIG. 5B a very simple implementation in which surfaces 167a' of rotary elements 164a' and surfaces 167b' of rotary elements 164b' serve to position nest 500 in the first horizontal dimension. By rotating elements 164a' joined by axle 166a' counter-clockwise within boss 169a' and rotating elements 164b' joined by axle 166b' clockwise within boss 169b', Surfaces 163a' and 163b' may be made to face each other and thereby a nest of different length in the first horizontal dimension may be positioned and accurately located between elements 164a' and 164b'.

Ganged elements 164a' and 164b' may be rotated manually about the axes of axles 166a' and 166b' respectively inside bosses 169a' and 169b' respectively. In some embodiments, the rotation of elements 164a' and 164b' may be done automatically by means of motorized drives controlled by controller 400 and suitable control software. That control may be based on predetermined dimensional data relating to the nest being positioned between the surfaces of elements 164a' and 164b'. It may also be based on input data derived from imaging data obtained from cameras 210 and/or 220. Further, the rotation may take place as nest 500 is lowered into position so that the particular surfaces of elements 164a' and 164b' destined to engage with the opposing ends of nest 500 along the first dimension may serve as closing horizontal grip on nest 500 as the surfaces rotate toward the position in which they face each other.

FIG. 5A and FIG. 5B show a further set of paired mutually counter-rotatable rotary positioning elements, not numbered for the sake of clarity, ganged similarly to rotary elements 164a' and 164b', and disposed to accurately locate nest 500 independently in the vertical dimension and in a second planar dimension of nest 500 perpendicular to the first dimension.

Figure 6:
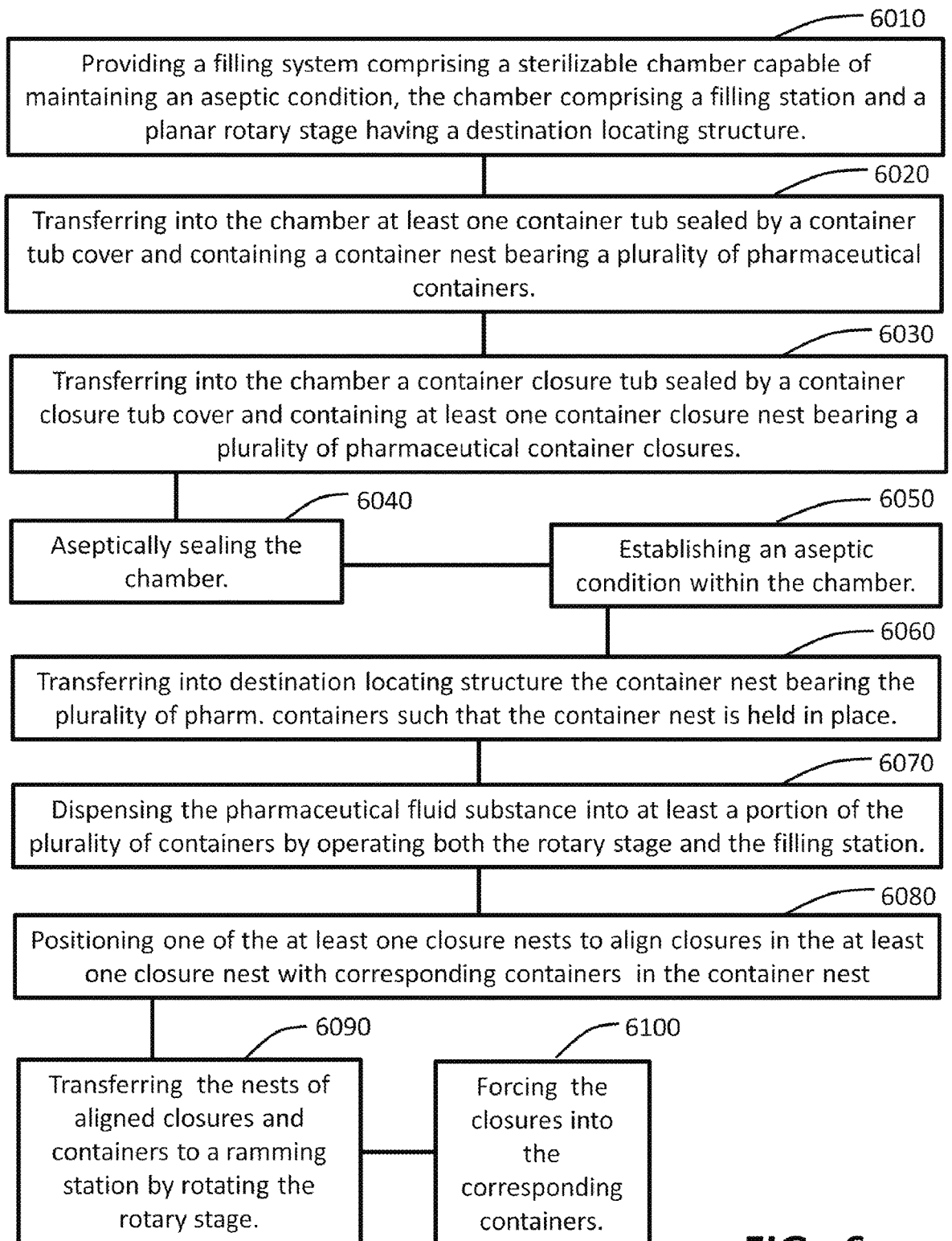
FIG. 6 shows a flow chart of a further method for filling nested pharmaceutical containers with a pharmaceutical fluid substance.

In a further aspect, described at the hand of FIG. 6, a method is provided for filling nested pharmaceutical containers 510 with a pharmaceutical fluid substance, the method comprising: providing [6010] filling system 1000 comprising sterilizable chamber 100 capable of maintaining an aseptic condition, chamber 100 comprising filling station 170 and planar rotary stage 130 having destination locating structure 136, 164a, 164b, 164a', 164b'; transferring [6020] into the chamber at least one container tub 530 sealed by container tub cover 520 and containing container nest 500 bearing a plurality of pharmaceutical containers 510; aseptically sealing [6040] chamber 100; establishing [6050] an aseptic condition within chamber 100; transferring [6060] into destination locating structure 136, 164a, 164b, 164a', 164b' container nest 500 bearing the plurality of pharmaceutical containers 510 such that container nest 500 is held in place; and dispensing [6070] the pharmaceutical fluid substance into at least a portion of the plurality of pharmaceutical containers 510 by operating both rotary stage 130 and filling station 170. Operating filling station 170 may include rotating filling station 170. Dispensing the pharmaceutical fluid substance may comprise dispensing the pharmaceutical fluid substance on an iterative and serial basis into containers 510.

Providing [6010] filling system 1000 may comprise providing filing apparatus comprising at least one cover removal station 140 within chamber 100 and wherein the transferring into destination locating structure container tub 530 comprises removing container tub cover 520 from container tub 530 by operating both rotary stage 130 and the at least one cover removal station 140. Operating the at least one cover removal station 140 may comprise rotating the at least one cover removal station 140. Providing [6010] filling system 1000 may comprise providing within chamber 100 at least one cover removal station 140 having engagement tool 142, transferring [6020] into chamber 100 at least one container tub 530 may comprise attaching to container tub 520 cover, cover removal fixture 540; and wherein the operating the at least one cover removal station 140 comprises engaging engagement tool 142 with cover removal fixture 540.

The method may further comprise transferring [6030] into the chamber container closure tub 630 sealed by a container closure tub cover and containing at least one container closure nest 600 bearing a plurality of pharmaceutical container closures 610. The method may further comprise positioning [6080] one of the at least one closure nests 600 to align closures 610 in the at least one closure nest 600 with corresponding containers 530 in container nest 500; transferring [6090] nests 500,600 of aligned closures 610 and containers 510 to a ramming station by rotating the rotary stage 130; and forcing [6100] closures 610 into corresponding containers 510. The method may further include adjusting tub locating structure 135,145 to accommodate a size of closure nest tub 630. Positioning [6080] one of the at least one closure nest 600 may comprise: obtaining image information about the one of the at least one closure nests 600; and positioning the one of the at least one closure nests 600 based on the image information. Positioning [6080] one of the at least one closure nest 600 may comprise: applying a vacuum to suction cups 162, 152*a*, 152*b*, 152*a'*, 152*b'*; lifting container closure nest 600 with the suction cups; and operating rotary stage 130.

Transferring [6020] into destination locating opening container nest 500 may comprise: applying a vacuum to the suction cups; lifting container nest 500 with the suction cups; and operating rotary stage 130. The method may further include selecting one of a plurality of sets of suction cups and wherein the applying a vacuum to suction cups is performed for the selected set of suction cups. The selecting may include rotating one of the plurality of sets of suction cups into position. The method may further include destination locating structure 136, 164*a*, 164*b*, 164*a'*, 164*b'* to accommodate a size of container nest 500. Adjusting may be performed in two at least generally orthogonal directions. The method may further include adjusting tub locating structure 139,149 to accommodate a size of container nest tub 530.

In a further aspect, a method is provided (see FIG. 1G) for removing within a controlled environment enclosure a container cover from a sealed container, for example tub 530 or tub 630, the sealed container being sealed by the container cover, for example cover 520, the method comprising: providing the container in controlled environment enclosure 100 with cover 520 sealed to a sealing surface of a lip of the container to seal the contents of the container against decontamination, cover 520 having cover removal fixture 540, decontaminating the sealed container in controlled environment enclosure 100, engaging cover removal fixture 540 with engagement tool 142, and removing the cover from the container using engagement tool 142. Engaging may engage cover removal fixture 540 with fork-shaped engagement tool 142. Engaging may engage a ball-shaped appendage on cover removal fixture 540.

Providing may include providing sterilized pharmaceutical containers 510 or closures 610 in the sealed container, for example tub 530 or 630, before the decontaminating. Attaching may take place before the container is in the controlled environment enclosure 100. Decontaminating the sealed container in controlled environment enclosure 100 may take place before the removing of cover 520. Removing cover 520 may include moving engagement tool 142 relative to container 530. Removing cover 520 may include moving both container 530 and engagement tool 142. The method may further comprise attaching cover removal fixture 540 to cover 520 before providing container 530 in the controlled environment enclosure.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An automated system for filling nested pharmaceutical containers with a pharmaceutical fluid substance, the system comprising a gloveless sterilizable environment capable of maintaining an aseptic condition, the system comprising:
   a closed, gloveless isolator chamber;
   a container filling system disposed in the gloveless isolator chamber, the container filling system having a dispensing head for filling the containers;
   a container closing system disposed within the gloveless isolator chamber, the container closing system having a plurality of rams for pushing closures into openings of the nested containers;
   a container manipulation mechanism disposed within the gloveless isolator chamber, the container manipulation mechanism capable of positioning the nested pharmaceutical containers within the gloveless isolator chamber including operably disposing the nested pharmaceutical containers with the container filling system and the container closing system,
   a vision system disposed within the gloveless isolator chamber having a view area including the range of motion of the container manipulation mechanism, and
   a controller coupled with the vision system for controlling the movement, filling, and closing of the nested containers within the gloveless isolator chamber, and
   a planar rotary stage having a rotary stage rotation axis, the rotary stage including a plurality of locating structures positioned with respect to the rotary stage at different positions around the rotary stage rotation axis, for holding nests of pharmaceutical container parts at the different positions around the rotary stage rotation axis, the rotary stage including a plurality of locating structures including surfaces associated with a first tub-holding opening in a rotary stage for holding a first tub containing at least one nest of containers, surfaces associated with a second tub-holding opening in the rotary stage for holding a second tub containing at least one nest of closures, and surfaces associated with a destination nest-holding opening in the rotary stage for holding at least one nest wherein at least one of the locating structures includes a reconfigurable locating structure with one or more adjustable positioning surfaces to position a tub with respect to the rotary stage, wherein the reconfigurable locating structure includes at least one pair of a reconfigurable stopping member and a restraining member disposed opposite each other across an opening in the rotary stage to precisely position at a first predetermined position a tub that contains at least one nest, wherein the stopping member is adjustable to stop the tub at the first predetermined position by a rotary adjustment and the restraining member is disposed to restrain the tub in the first predetermined position.

2. The system of claim 1 wherein at least a first of the reconfigurable locating structures includes a rotary positioning element having an axis of rotation parallel to a plane of the rotary stage and includes a plurality of different positioning surfaces that are selectable by rotating the rotary positioning element, or at least one of the reconfigurable locating structures includes a pair of opposing rotary positioning elements each having an axis of rotation parallel to a plane of the rotary stage and each including a plurality of different positioning surfaces that are selectable by rotating that rotary positioning elements, to accommodate different nest widths, or at least one of the reconfigurable locating structures includes at least a first pair of opposing positioning elements that define positioning surfaces that oppose each other along a first positioning axis that is at least generally parallel to a plane of the rotary stage and at least a second pair of opposing positioning elements that define positioning surfaces that oppose each other along a second positioning axis that is at least generally parallel to a plane of the rotary stage and at least generally perpendicular to the first positioning axis.

3. The system of claim 2 wherein at least one of the positioning elements in each of the first and second pairs of positioning elements includes a rotary positioning element having an axis of rotation parallel to a plane of the rotary stage and including a plurality of different positioning surfaces.

4. The system of claim 1 further including at least one cover removal station positioned to remove covers from tubs containing at least one nest of pharmaceutical packaging materials held in one of the locating structures, wherein the at least one cover removal station is rotatable about a cover removal station rotation axis parallel to the rotary stage rotation axis to remove the tub covers in combination with rotation of the rotary stage, and the at least one cover removal station comprises an engagement tool disposed and configured to engage with a cover removal fixture on the tub cover.

5. The system of claim 4 wherein the controller is operative to instruct the rotary stage to rotate to angular positions that are one of predetermined and based on the image information and to control the at least one cover removal station, the filling station, the container closing system to operate in conjunction with the rotary stage.

6. The system of claim 1 wherein the filling station is configured to be rotatable about a filling station rotation axis parallel to the rotary stage rotation axis to position in combination with rotation of the rotary stage the dispenser head over any one of the plurality of pharmaceutical containers held by one of the one of the locating structures.

7. The system of claim 1 wherein the vision system includes at least one camera disposed to obtain image information about at least one of the nests of pharmaceutical container parts.

8. The system of claim 1 further comprising a ram system configured for forcing nested closures into corresponding nested containers.

9. The system of claim 1 further including at least one cover removal station positioned to remove covers from tubs containing at least one nest of pharmaceutical packaging materials held in one of the locating structures, wherein the at least one cover removal station is rotatable about a cover removal station rotation axis parallel to the rotary stage rotation axis to remove the tub covers in combination with rotation of the rotary stage, and the at least one cover removal station comprises an engagement tool disposed and configured to engage with a cover removal fixture on the tub cover.

10. The system of claim 1 wherein the filling station is configured to be rotatable about a filling station rotation axis parallel to the rotary stage rotation axis to position in combination with rotation of the rotary stage the dispenser head over any one of the plurality of pharmaceutical containers held by one of the one of the locating structures.

11. The system of claim 1 wherein the vision system includes at least one camera disposed to obtain image information about at least one of the nests of pharmaceutical container parts.

12. The system of claim 1 further comprising a ram system configured for forcing nested closures into corresponding nested containers.

13. The system of claim 1 wherein the controller is operative to instruct the rotary stage to rotate to angular positions that are one of predetermined and based on the image information and to control the at least one cover removal station, the filling station, the container closing system to operate in conjunction with the rotary stage.

14. An automated system for filling nested pharmaceutical containers with a pharmaceutical fluid substance, the system comprising a gloveless sterilizable chamber environment capable of maintaining an aseptic condition, the system comprising:
  a closed, gloveless isolator chamber;
  a container filling system disposed in the gloveless isolator chamber, the container filling system having a dispensing head for filling the containers;
  a container closing system disposed within the gloveless isolator chamber, the container closing system having a plurality of rams for pushing closures into openings of the nested containers;
  a container manipulation mechanism disposed within the gloveless isolator chamber, the container manipulation mechanism capable of positioning the nested pharmaceutical containers within the gloveless isolator chamber including operably disposing the nested pharmaceutical containers with the container filling system and the container closing system,
  a vision system disposed within the gloveless isolator chamber having a view area including the range of motion of the container manipulation mechanism,
  a controller coupled with the vision system for controlling the movement, filling, and closing of the nested containers within the gloveless isolator chamber, and
  a planar rotary stage having a rotary stage rotation axis, the rotary stage including a plurality of locating structures positioned with respect to the rotary stage at different positions around the rotary stage rotation axis, for holding nests of pharmaceutical container parts at the different positions around the rotary stage rotation axis, the rotary stage including a plurality of locating structures including surfaces associated with a first tub-holding opening in a rotary stage for holding a first tub containing at least one nest of containers, surfaces associated with a second tub-holding opening in the rotary stage for holding a second tub containing at least one nest of closures, and surfaces associated with a destination nest-holding opening in the rotary stage for holding at least one nest, wherein the container manipulation mechanism further comprises at least one vacuum pickup system comprising suction cups disposed to engage with at least one of a container nest and a closure nest held on a rotary stage, the at least one vacuum pickup system being configured in combination with rotation of the rotary stage to lift a pharmaceutical container nest from a pharmaceutical container tub and to deposit the pharmaceutical container nest in the destination opening in combination with rotation of the rotary stage and to lift a pharmaceutical container closure nest from a pharmaceutical container closure tub and to deposit the container closure nest on top of the pharmaceutical container nest.

15. The system of claim 14 wherein the vacuum pickup system includes a reconfigurable vacuum pickup system comprising:
a first set of suction cups arranged in a first pattern,
a second set of suction cups arranged in a second pattern different from the first pattern, and
a selection mechanism operative to position either the first set of suction cups or the second set of suction cups to engage with the at least a first of the nests of pharmaceutical container parts while it is held by one of the plurality of locating structures, wherein the selection mechanism of the reconfigurable vacuum pickup system includes a rotary mechanism operative to position the first or second sets of suction cups in an engagement position.

16. An automated system for filling nested pharmaceutical containers with a pharmaceutical fluid substance, the system comprising a gloveless sterilizable environment capable of maintaining an aseptic condition, the system comprising:
a closed, gloveless isolator chamber;
a sterilization system operably coupled to the gloveless isolator chamber;
a container filling system disposed in the gloveless isolator chamber, the container filling system having a dispensing head for filling the containers;
a container closing system disposed within the gloveless isolator chamber, the container closing system having a plurality of rams for pushing closures into openings of the nested containers;
a container manipulation mechanism disposed within the gloveless isolator chamber, the container manipulation mechanism capable of positioning the nested pharmaceutical containers within the gloveless isolator chamber including operably disposing the nested pharmaceutical containers with the container filling system and the container closing system;
a vision system disposed within the gloveless isolator chamber having a view area including the range of motion of the container manipulation mechanism, and a controller coupled with the vision system for controlling the movement, filling, and closing of the nested containers within the gloveless isolator chamber; and a planar rotary stage having a rotary stage rotation axis, the rotary stage including a plurality of locating structures positioned with respect to the rotary stage at different positions around the rotary stage rotation axis, for holding nests of pharmaceutical container parts at the different positions around the rotary stage rotation axis, wherein the rotary stage includes a plurality of locating structures including surfaces associated with a first tub-holding opening in a rotary stage for holding a first tub containing at least one nest of containers, surfaces associated with a second tub-holding opening in the rotary stage for holding a second tub containing at least one nest of closures, and surfaces associated with a destination nest-holding opening in the rotary stage for holding at least one nest.

17. The system of claim 16 wherein the container manipulation mechanism further comprises at least one vacuum pickup system comprising suction cups disposed to engage with at least one of a container nest and a closure nest held on a rotary stage, the at least one vacuum pickup system being configured in combination with rotation of the rotary stage to lift a pharmaceutical container nest from a pharmaceutical container tub and to deposit the pharmaceutical container nest in the destination opening in combination with rotation of the rotary stage and to lift a pharmaceutical container closure nest from a pharmaceutical container closure tub and to deposit the container closure nest on top of the pharmaceutical container nest.

18. The system of claim 17 wherein the vacuum pickup system includes a reconfigurable vacuum pickup system comprising:
a first set of suction cups arranged in a first pattern,
a second set of suction cups arranged in a second pattern different from the first pattern, and
a selection mechanism operative to position either the first set of suction cups or the second set of suction cups to engage with the at least a first of the nests of pharmaceutical container parts while it is held by one of the plurality of locating structures, wherein the selection mechanism of the reconfigurable vacuum pickup system includes a rotary mechanism operative to position the first or second sets of suction cups in an engagement position.

19. The system of claim 16 wherein at least one of the locating structures includes a reconfigurable locating structure with one or more adjustable positioning surfaces to position a tub with respect to the rotary stage, wherein the reconfigurable locating structure includes at least one pair of a reconfigurable stopping member and a restraining member disposed opposite each other across an opening in the rotary stage to precisely position at a first predetermined position a tub that contains at least one nest, wherein the stopping member is adjustable to stop the tub at the first predetermined position by a rotary adjustment and the restraining member is disposed to restrain the tub in the first predetermined position.

20. The system of claim 19 wherein at least a first of the reconfigurable locating structures includes a rotary positioning element having an axis of rotation parallel to a plane of the rotary stage and includes a plurality of different positioning surfaces that are selectable by rotating the rotary positioning element, or at least one of the reconfigurable locating structures includes a pair of opposing rotary positioning elements each having an axis of rotation parallel to a plane of the rotary stage and each including a plurality of different positioning surfaces that are selectable by rotating that rotary positioning elements, to accommodate different nest widths, or at least one of the reconfigurable locating structures includes at least a first pair of opposing positioning elements that define positioning surfaces that oppose each other along a first positioning axis that is at least generally parallel to a plane of the rotary stage and at least a second pair of opposing positioning elements that define positioning surfaces that oppose each other along a second positioning axis that is at least generally parallel to a plane of the rotary stage and at least generally perpendicular to the first positioning axis.

21. The system of claim 20 wherein at least one of the positioning elements in each of the first and second pairs of positioning elements includes a rotary positioning element having an axis of rotation parallel to a plane of the rotary stage and including a plurality of different positioning surfaces.

22. The system of claim 16 further including at least one cover removal station positioned to remove covers from tubs containing at least one nest of pharmaceutical packaging materials held in one of the locating structures, wherein the at least one cover removal station is rotatable about a cover removal station rotation axis parallel to the rotary stage rotation axis to remove the tub covers in combination with rotation of the rotary stage, and the at least one cover removal station comprises an engagement tool disposed and configured to engage with a cover removal fixture on the tub cover.

23. The system of claim 16 wherein the filling station is configured to be rotatable about a filling station rotation axis parallel to the rotary stage rotation axis to position in combination with rotation of the rotary stage the dispenser head over any one of the plurality of pharmaceutical containers held by one of the one of the locating structures.

24. The system of claim 16 wherein the vision system includes at least one camera disposed to obtain image information about at least one of the nests of pharmaceutical container parts.

25. The system of claim 16 further comprising a ram system configured for forcing nested closures into corresponding nested containers.

26. The system of claim 25 wherein the controller is operative to instruct the rotary stage to rotate to angular positions that are one of predetermined and based on the image information and to control the at least one cover removal station, the filling station, the container closing system to operate in conjunction with the rotary stage.

* * * * *